US009085579B2

(12) United States Patent
Stoessel et al.

(10) Patent No.: US 9,085,579 B2
(45) Date of Patent: Jul. 21, 2015

(54) MATERIALS FOR ORGANIC ELECTROLUMINESCENT DEVICES

(75) Inventors: Philipp Stoessel, Frankfurt (DE);
Holger Heil, Frankfurt am Main (DE);
Dominik Joosten, Frankfurt (DE);
Christof Pflumm, Frankfurt (DE); Anja Gerhard, Egelsbach (DE)

(73) Assignee: Merck Patent GmbH (DE)

( * ) Notice: Subject to any disclaimer, the term of this patent is extended or adjusted under 35 U.S.C. 154(b) by 981 days.

(21) Appl. No.: 13/255,782

(22) PCT Filed: Feb. 15, 2010

(86) PCT No.: PCT/EP2010/000913
§ 371 (c)(1),
(2), (4) Date: Sep. 9, 2011

(87) PCT Pub. No.: WO2010/102709
PCT Pub. Date: Sep. 16, 2010

(65) Prior Publication Data
US 2011/0315933 A1     Dec. 29, 2011

(30) Foreign Application Priority Data
Mar. 13, 2009 (DE) .......................... 10 2009 013 041

(51) Int. Cl.
*H01L 51/54* (2006.01)
*C09K 11/06* (2006.01)
*C07D 471/16* (2006.01)
*C07F 15/00* (2006.01)
*C09B 57/00* (2006.01)
*C09B 57/10* (2006.01)
*C09B 1/00* (2006.01)
*H01L 51/00* (2006.01)

(52) U.S. Cl.
CPC .......... *C07D 471/16* (2013.01); *C07F 15/0033* (2013.01); *C07F 15/0086* (2013.01); *C09B 1/00* (2013.01); *C09B 57/00* (2013.01); *C09B 57/10* (2013.01); *C09K 11/06* (2013.01); *H01L 51/0085* (2013.01); *H01L 51/0087* (2013.01); C09K 2211/1022 (2013.01); C09K 2211/1044 (2013.01); C09K 2211/1074 (2013.01); C09K 2211/185 (2013.01); H01L 51/006 (2013.01); H01L 51/0081 (2013.01); Y02E 10/549 (2013.01)

(58) Field of Classification Search
CPC . C07D 471/16; C07F 15/002; C07F 15/0033; C07F 15/0046; C07F 15/006; C07F 15/0073; C07F 15/0086; C07F 9/547; C07F 9/553; C07F 9/645; C07F 9/6515; C07F 9/6524; C07F 9/6558; C07F 9/6561; C09B 1/00; C09B 57/00; C09B 57/10; H01B 1/12; H01L 51/006; H01L 51/0061; H01L 51/0084–51/0089; C09K 11/06; C09K 2211/1022; C09K 2211/1044; C09K 2211/1055; C09K 2211/1059; C09K 2211/107; C09K 2211/1074; C09K 2211/181; C09K 2211/183; C09K 2211/185; C09K 2211/187; C09K 2211/188

See application file for complete search history.

(56) References Cited

U.S. PATENT DOCUMENTS

| | | | |
|---|---|---|---|
| 4,539,507 A | 9/1985 | VanSlyke et al. | |
| 5,151,629 A | 9/1992 | VanSlyke | |
| 5,621,131 A | 4/1997 | Kreuder et al. | |
| 6,653,438 B1 | 11/2003 | Spreitzer et al. | |
| 2005/0069729 A1 | 3/2005 | Ueda et al. | |
| 2005/0227112 A1* | 10/2005 | Ise et al. | 428/690 |
| 2006/0134461 A1 | 6/2006 | Huo et al. | |
| 2006/0175958 A1 | 8/2006 | Gerhard et al. | |
| 2006/0208221 A1 | 9/2006 | Gerhard et al. | |
| 2006/0255332 A1 | 11/2006 | Becker et al. | |
| 2006/0284140 A1 | 12/2006 | Breuning et al. | |
| 2007/0060736 A1 | 3/2007 | Becker et al. | |
| 2007/0082284 A1 | 4/2007 | Stoessel et al. | |
| 2007/0103060 A1 | 5/2007 | Itoh et al. | |
| 2007/0176147 A1 | 8/2007 | Buesing et al. | |
| 2007/0205714 A1 | 9/2007 | Busing et al. | |
| 2009/0134384 A1 | 5/2009 | Stoessel et al. | |
| 2009/0167166 A1 | 7/2009 | Bach et al. | |
| 2009/0226759 A1 | 9/2009 | Heun et al. | |
| 2009/0302742 A1 | 12/2009 | Komori et al. | |
| 2009/0302752 A1 | 12/2009 | Parham et al. | |
| 2010/0102305 A1 | 4/2010 | Heun et al. | |
| 2010/0187977 A1 | 7/2010 | Kai et al. | |
| 2010/0244009 A1 | 9/2010 | Parham et al. | |
| 2010/0288974 A1 | 11/2010 | Buesing et al. | |
| 2011/0068304 A1 | 3/2011 | Parham et al. | |
| 2011/0105778 A1 | 5/2011 | Stoessel et al. | |
| 2011/0108822 A1* | 5/2011 | Parham et al. | 257/40 |
| 2011/0121274 A1 | 5/2011 | Parham et al. | |
| 2011/0140043 A1 | 6/2011 | Stoessel et al. | |

FOREIGN PATENT DOCUMENTS

| | | |
|---|---|---|
| DE | 102008033943 | 1/2010 |
| DE | 102008036982 | 2/2010 |
| DE | 102008056688 | 5/2010 |
| EP | 0 707 020 | 4/1996 |
| EP | 0 842 208 | 5/1998 |
| EP | 0 894 107 | 2/1999 |
| EP | 1 028 136 | 8/2000 |
| EP | 1205527 | 5/2002 |
| EP | 1617710 | 1/2006 |
| EP | 1617711 | 1/2006 |
| EP | 1731584 | 12/2006 |
| JP | 2004/288381 | 10/2004 |
| JP | 2005-347160 | 12/2005 |

(Continued)

*Primary Examiner* — Michael H Wilson
(74) *Attorney, Agent, or Firm* — Drinker Biddle & Reath LLP

(57) ABSTRACT

The present invention relates to metal complexes of the general formulae I to V, in particular as emitter molecules in organic electronic devices, to ligands of the general formulae Ia to Va, and to the use thereof for the preparation of metal complexes, to a layer and an electronic device which comprise the compounds according to the invention, and to a process for the preparation of the compounds according to the invention.

15 Claims, No Drawings

(56) References Cited

FOREIGN PATENT DOCUMENTS

| WO | WO-92/18552 | 10/1992 |
| --- | --- | --- |
| WO | WO-00/22026 | 4/2000 |
| WO | WO-2004/041901 | 5/2004 |
| WO | WO-2004/070772 | 8/2004 |
| WO | WO-2004/093207 | 10/2004 |
| WO | WO-2004/108857 | 12/2004 |
| WO | WO-2004/113412 | 12/2004 |
| WO | WO-2004/113468 | 12/2004 |
| WO | WO-2005/003253 | 1/2005 |
| WO | WO-2005/011013 | 2/2005 |
| WO | WO-2005/014689 | 2/2005 |
| WO | WO-2005/039246 | 4/2005 |
| WO | WO-2005/040302 | 5/2005 |
| WO | WO-2005/042444 | 5/2005 |
| WO | WO-2005/042550 | 5/2005 |
| WO | WO-2005/104264 | 11/2005 |
| WO | WO-2005/111172 | 11/2005 |
| WO | WO-2006/061181 | 6/2006 |
| WO | WO-2006/117052 | 11/2006 |
| WO | WO-2007/017066 | 2/2007 |
| WO | WO-2007/063754 | 6/2007 |
| WO | WO-2007/137725 | 12/2007 |
| WO | WO-2008/056746 | 5/2008 |
| WO | WO-2008/086851 | 7/2008 |
| WO | WO-2009/062578 | 5/2009 |

* cited by examiner

MATERIALS FOR ORGANIC ELECTROLUMINESCENT DEVICES

CROSS-REFERENCE TO RELATED APPLICATIONS

This application is a national stage application (under 35 U.S.C. §371) of PCT/EP2010/000913, filed Feb. 15, 2010, which claims benefit of German application 10 2009 013 041.1, filed Mar. 13, 2009.

BACKGROUND OF THE INVENTION

The present invention relates to transition-metal complexes of the general formulae I to V, in particular as emitter molecules in organic electronic devices, to ligands of the general formulae Ia to Va, and to the use thereof for the preparation of a metal complex, to a layer and an electronic device which comprise the compounds according to the invention, and to a process for the preparation of the compounds according to the invention.

Chelate complexes and organometallic compounds are used as functional materials in a number of applications of different types which can be ascribed to the electronics industry in the broadest sense. In the case of organic electroluminescent devices based on organic components (general description of the structure cf. U.S. Pat. No. 4,539,507 and U.S. Pat. No. 5,151,629) and individual components thereof, organic light-emitting diodes (OLEDs), there is still a further need for improvement in spite of the successes that have already been achieved.

In recent years, organometallic complexes which exhibit phosphorescence instead of fluorescence have increasingly been under discussion (M. A. Baldo, S. Lamansky, P. E. Burrows, M. E. Thompson, S. R. Forrest, Appl. Phys. Lett., 1999, 75, 4-6). For theoretical spin-statistical reasons, an up to four-fold increase in energy and power efficiency is possible using organometallic compounds as phosphorescence emitters. The main conditions that should be mentioned here for practical use are, in particular, a long operating lifetime, high stability to temperature stresses, a low use and operating voltage in order to facilitate mobile applications, and high colour purity.

Besides the individual specific weak points for each material, the class of known metal complexes has general weak points, which are described briefly below:

Many of the known metal complexes have low thermal stability. On vacuum deposition, this always results in the liberation of organic pyrolysis products, which, in some cases even in small amounts, considerably shorten the operating lifetime of OLEDs.

The interaction of the complex units in the solid, in particular in the case of planar complexes of $d^8$ metals, such as platinum(II), likewise causes aggregation of the complex units in the emitter layer if the degree of doping exceeds about 0.1%, which is the case in accordance with the current prior art. This aggregation results in the formation of so-called excimers or exciplexes on excitation (optical or electrical). These aggregates frequently have an unstructured, broad emission band, which makes the generation of pure primary colours (RGB) considerably more difficult or completely impossible. In general, the efficiency for this transition also drops.

In addition, it is evident from the above-said that the emission colour is highly dependent on the degree of doping, a parameter which can be controlled precisely only with considerable technical effort, in particular in large production plants.

To date, no blue-phosphorescent metal complexes are known which meet the requirements for high-quality and long-lived products, in particular with respect to the lifetime and the colour coordinates.

Known in OLED technology are metal complexes of the group 10 transition metals (Ni, Pd, Pt) in which the central metal is bonded via two aromatic N atoms and two C atoms (WO 2004/108857, WO 2005/042550, WO 2005/042444, US 2006/0134461 A1) or two imine-like N atoms in combination with two phenolic O atoms (WO 2004/108857) or via two aromatic N atoms and two basic N atoms (WO 2004/108857). The known compounds have, inter alia, electroluminescence in the blue, red and green region of the electromagnetic spectrum.

Nevertheless, there is still a demand for further compounds which do not have the above-mentioned disadvantages and preferably exhibit electroluminescence in the blue, red and green region of the electromagnetic spectrum and, if desired, can also be employed in the solid state as light-emitting layer.

BRIEF SUMMARY OF THE INVENTION

The object of the invention was thus to provide compounds of this type.

Surprisingly, it has been found that the complexes described below containing amine-like N atoms, also in combination with aromatic C atoms, achieve a long operating lifetime as phosphorescence emitters in OLEDs, and achieve high stability to temperature stresses and a low use and operating voltage by bridging these ligands.

In order to achieve the object mentioned, the present invention provides compounds of the general formula I

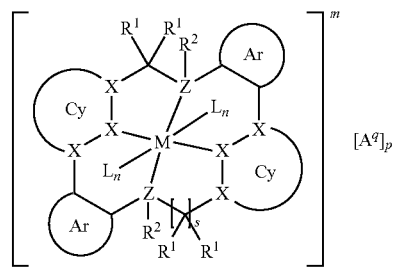

formula I

DETAILED DESCRIPTION OF THE INVENTION

The symbols and indices used in formula I have the following meanings:

M is a metal or a metal ion;

L is, identically or differently on each occurrence, a neutral, cationic or anionic ligand;

X is, identically or differently on each occurrence, C or N;

Z is, identically or differently on each occurrence, N or P;

Cy is, identically or differently on each occurrence, a mono- or polycyclic non-aromatic ring system having 4 to 60 ring atoms, which may be substituted by one or more radicals $R^1$, or a mono- or polycyclic aryl or heteroaryl group having 5 to 60 ring atoms, which may in each case be substituted by one or more radicals $R^1$, with the proviso that the atoms denoted by X are constituents of the cyclic group Cy;

Ar is, identically or differently on each occurrence, a mono- or polycyclic aryl or heteroaryl group having 5 to 60 ring atoms, which may be substituted by one or more radicals $R^1$, with the proviso that the C atoms which bond to X or Z are constituents of the group Ar;

$R^1$ is, identically or differently on each occurrence, selected from the group consisting of H, D, F, Cl, Br, I, CN, $NO_2$, a straight-chain $C_{1-40}$-alkyl group, $C_{1-40}$-alkoxy group or thio-$C_{1-40}$-alkyl group or a branched or cyclic $C_{3-40}$-alkyl group, $C_{3-40}$-alkoxy group or thio-$C_{3-40}$-alkoxy group, each of which may be substituted by one or more radicals $R^3$, where one or more non-adjacent $CH_2$ groups may be replaced by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$, and where one or more H atoms may be replaced by D, F, Cl, Br, I, CN or $NO_2$, a mono- or polycyclic aromatic or heteroaromatic ring system having 5 to 60 aromatic ring atoms, which may in each case be substituted by one or more radicals $R^4$, where, in the case where two adjacent $R^1$ in each case form an aromatic or heteroaromatic ring system, these two ring systems may be linked to one another by a single bond or a divalent unit G, an aryloxy or heteroaryloxy group having 5 to 60 aromatic ring atoms, which may be substituted by one or more radicals $R^4$, and a combination of these groups, where one of the $R^1$ may be linked to an L, forming a penta- or hexadentate ligand; or where one of the $R^1$ may be linked to an L and an opposite $R^1$ or $R^2$, forming a penta- or hexadentate ligand in the form of a cage; or two adjacent $R^1$ together form an oxo group =O, a group =NH or a group $=NR^5$, or two adjacent $R^1$, together with the atom or atoms to which they are bonded, form a 5- or 6-membered aliphatic or aromatic ring, which may be substituted by one or more radicals $R^4$, where one or more of the ring $CH_2$ groups may be replaced by O, S or NR;

$R^2$ is, identically or differently on each occurrence, selected from the group consisting of a non-bonding electron pair, H, D, a straight-chain $C_{1-40}$-alkyl group, $C_{1-40}$-alkoxy group or thio-$C_{1-40}$-alkyl group or a branched or cyclic $C_{3-40}$-alkyl group, $C_{3-40}$-alkoxy group or thio-$C_{3-40}$-alkoxy group, each of which may be substituted by one or more radicals $R^3$, where one or more non-adjacent $CH_2$ groups may be replaced by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$, and where one or more H atoms may be replaced by D, F, Cl, Br, I, CN or $NO_2$, a mono- or polycyclic aromatic or heteroaromatic ring system having 5 to 60 ring atoms, which may in each case be substituted by one or more radicals $R^4$, an aryloxy or heteroaryloxy group having 5 to 60 aromatic ring atoms, which may be substituted by one or more radicals $R^4$, and a combination of these groups; or in the case where Z is equal to N, $R^2$ may furthermore be equal to O, in which case an amine oxide is formed;

$R^3$ is, identically or differently on each occurrence, a mono- or polycyclic aromatic or heteroaromatic ring system having 5 to 30 ring atoms, in which one or more H atoms may be replaced by D, F, Cl, Br, I, CN or $NO_2$, where, in the case where two adjacent $R^3$ in each case form an aromatic or heteroaromatic ring system, these two ring systems may be linked to one another by a single bond or a divalent unit G;

$R^4$ is, identically or differently on each occurrence, selected from the group consisting of F, Cl, Br, I, CN, a straight-chain $C_{1-20}$-alkyl group or a branched or cyclic $C_{3-20}$-alkyl group, or two adjacent $R^4$, together with the atoms to which they are bonded, form a 5-, 6-, 7- or 8-membered aliphatic ring, where one or more of the ring $CH_2$ groups may be replaced by O, S or NR;

$R^5$ is selected from the group consisting of H, D, a straight-chain $C_{1-20}$-alkyl group or a branched or cyclic $C_{3-20}$-alkyl group, in which in each case one or more H atoms may be replaced by D, F, Cl, Br, I, CN or $NO_2$, a mono- or polycyclic aromatic or heteroaromatic ring system having 5 to 30 ring atoms, in which one or more H atoms may be replaced by D, F, Cl, Br, I, CN or $NO_2$, where, in the case where two adjacent $R^5$ in each case form an aromatic or heteroaromatic ring system, these two ring systems may be linked to one another, or two adjacent $R^5$, together with the atoms to which they are bonded, form a 5-, 6-, 7- or 8-membered aliphatic ring, where one or more of the ring $CH_2$ groups may be replaced by O, S or NR;

G represents a divalent unit which is selected from the group consisting of $C(R^5)_2$, $C(R^5)_2—C(R^5)_2$, $C=O$, $NR^5$, $PR^5$, O and S;

n is, identically or differently on each occurrence, 0 or 1;

m denotes the charge of the complex and can be +4, +3, +2, +1, 0, −1, −2, −3 or −4;

$A^q$ is any desired counterion, where q represents the charge of A and can be −4, −3, −2, −1, 0, +1, +2, +3 or +4;

p is 0, 1, 2, 3 or 4;

s is 0 or 1, where, for s=0, a further group $R^2$ is also bonded to the corresponding Z and a group $R^1$ is also bonded to the corresponding X.

m, q and p here are selected so that overall a charge-neutral compound is formed, i.e. the product of the index p with the charge q of the counterion is equal to the charge m of the complex.

The following general definitions are furthermore used within this invention:

For the purposes of this invention, a mono- or polycyclic non-aromatic ring system is preferably taken to mean an aliphatic ring system having 4 to 60 ring atoms, preferably 5 to 20 ring atoms, particularly preferably 5 or 6 ring atoms, which may contain up to three, preferably up to 2, particularly preferably 0, 1 or 2, heteroatoms selected from N, O, S, preferably N. Examples according to the invention are 1,2-diazacyclopentane and preferably 1,3-diazacyclopentane.

For the purposes of this invention, an aryl group contains 6 to 60 C atoms; for the purposes of this invention, a heteroaryl group contains 1 to 59 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, pyrene, quinoline, isoquinoline, etc.

For the purposes of this invention, a mono- or polycyclic aromatic ring system is preferably taken to mean an aromatic ring system having 6 to 60 carbon atoms, preferably 6 to 30 carbon atoms, particularly preferably 6 to 12 carbon atoms. For the purposes of the present invention, an aromatic ring system is intended to be taken to mean a system which does not necessarily contain only aromatic groups, but instead in which, in addition, a plurality of aromatic groups may be connected by a short non-aromatic unit (<10% of the atoms other than H), such as, for example, C, O, N, etc. These aromatic ring systems may be monocyclic or polycyclic, i.e. they may contain one ring (for example phenyl) or two or more rings, which may also be condensed (for example naphthyl), or may be covalently bonded (for example biphenyl), or contain a combination of condensed and linked rings.

Preferred aromatic ring systems are, for example, benzene, biphenyl, terphenyl, naphthalene, anthracene, binaphthyl, phenanthrene, benzanthracene, benzophenanthrene, dihydrophenanthrene, pyrene, dihydropyrene, chrysene, perylene, tetracene, pentacene, benzopyrene, fluorene and indene.

For the purposes of this invention, a mono- or polycyclic heteroaromatic ring system is preferably taken to mean a heteroaromatic ring system having 5 to 60 ring atoms, preferably 5 to 30 ring atoms, particularly preferably 5 to 14 ring atoms. The heteroaromatic ring system contains at least one heteroatom selected from N, O and S (the remaining atoms are carbon). A heteroaromatic ring system is in addition intended to be taken to mean a system which does not necessarily contain only aromatic or heteroaromatic groups, but instead in which, in addition, a plurality of aromatic or heteroaromatic groups may be connected by a short non-aromatic unit (<10% of the atoms other than H), such as, for example, C, O, N, etc. These heteroaromatic ring systems may be monocyclic or polycyclic, i.e. they can contain one ring (for example pyridyl) or two or more rings, which may also be condensed or covalently bonded, or contain a combination of condensed and linked rings.

Preferred heteroaromatic ring systems are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, isobenzothiophene, dibenzothiophene, benzothiadiazothiophene, or combinations of these groups. Particular preference is given to imidazole, benzimidazole and pyridine.

The mono- or polycyclic non-aromatic, aromatic or heteroaromatic ring systems, aryl groups and heteroaryl groups may carry one or more substituents, as described above.

An aryloxy or heteroaryloxy group having 5 to 60 aromatic ring atoms is taken to mean a group which carries, via an O atom, a mono- or polycyclic aromatic or heteroaromatic ring system having 5 to 60 ring atoms as defined above. The aryloxy or heteroaryloxy group may likewise carry one or more substituents, which are defined above.

For the purposes of the present invention, a straight-chain, branched or cyclic $C_{1-20}$-alkyl group or $C_{1-40}$-alkyl group is taken to mean an alkyl group having 1 to 20 or 1 to 40 C atoms respectively. Cyclic alkyl groups can be mono-, bi- or polycyclic alkyl groups. Individual —CH— or —CH$_2$— groups may be substituted by N, NH, O or S. Preference is given to the radicals methyl, ethyl, n-propyl, i-propyl, n-butyl, i-butyl, s-butyl, t-butyl, 2-methylbutyl, n-pentyl, s-pentyl, t-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl and 2,2,2-trifluoroethyl. Preferred alkenyl groups are ethenyl, propenyl, butenyl, pentenyl, cyclopentenyl, hexenyl, cyclohexenyl, heptenyl, cycloheptenyl, octenyl and cyclooctenyl. Preferred alkynyl groups are ethynyl, propynyl, butynyl, pentynyl, hexynyl, heptynyl and octynyl. A $C_1$- to $C_{40}$-alkoxy group or thioalkoxy group is preferably taken to mean methoxy, trifluoromethoxy, ethoxy, n-propoxy, i-propoxy, n-butoxy, i-butoxy, s-butoxy, t-butoxy or 2-methylbutoxy, and the corresponding sulfur analogues respectively. The alkyl groups, alkoxy groups and thioalkyl groups may in addition be substituted by one or more radicals $R^3$ as defined above.

A 5-, 6-, 7- or 8-membered aliphatic ring can be a ring which consists only of CH$_2$ units, but it is also possible for one or more of the CH$_2$ groups to be replaced by O, S or NR. It is optionally also possible for one or more of the H atoms to be replaced by a radical $R^4$ as defined above. Particular preference is given to cyclopentyl or 1,3-dioxocyclopentyl.

In a preferred embodiment of the invention, the metal M is a transition metal or transition-metal ion or a main-group metal or main-group metal ion.

If M is a transition metal or transition-metal ion, it is preferably selected from the group consisting of Mo, W, Ru, Os, Rh, Ir, Ni, Pd, Pt, Cu, Ag, Au and Zn. M can be uncharged or charged. If M is equal to Ni or Pd, it is preferably in the oxidation state +2. If M is equal to Pt, it is preferably in the oxidation state +2 or +4. If M is equal to Rh, Ir or Au, it is preferably in the oxidation state +3. Particular preference is given to complexes where M is equal to Ru, Os, Rh, Ir, Pd, Pt, Cu, Ag and Au, and extraordinary preference is given to Ir and Pt.

If M is a main-group metal or main-group metal ion, it is preferably selected from the group consisting of alkali metals, alkaline-earth metals, Al, Ga and In. If M is a main-group metal or main-group metal ion, the coordination of the cyclic ligand to the metal preferably takes place via four nitrogen atoms.

In a preferred embodiment of the invention, the symbol Z in compounds of the formula (I) stands for N.

The complex of the formula I can be charged or neutral. All charge numbers, depending on the oxidation state of the metal and the nature of the ligand, +4, +3, +2, +1, 0, −1, −2, −3 and −4 can occur here as denoted by the index m. The complex is preferably in the charge numbers +3 to −3, particularly preferably +2 to −2, more preferably +1 to −1 and very particularly preferably neutral. The symbol A denotes the corresponding counterion(s), which correspondingly occur(s) in the charge numbers −4, −3, −2, −1, 0, +1, +2, +3 or +4. This is expressed by the index q. The counterions may also occur more than once, as expressed by the index p. Possible counterions are metal complexes of the compound of the formula I which have a correspondingly opposite charge. Furthermore preferred counterions are alkali or alkaline-earth metal cations, iodide, bromide, chloride, cyanide, hexafluorophosphate and tetrafluoroborate.

The unit Cy is preferably an aryl or heteroaryl group or a cyclic carbene, selected from the group consisting of phenyl, naphthyl, anthracyl, phenanthryl, biphenyl, pyridyl, 1,3-diazolyl, which bonds to M as a carbene, 1,3-diazocyclopentyl, which bonds to M as a carbene, and benzo-1,3-diazolyl, which bonds to M as a carbene.

The unit Ar is preferably a unit selected from the group consisting of phenyl, naphthyl, anthracyl, phenanthryl and pyridyl, where these groups may each be substituted by one or more radicals $R^1$.

In a further embodiment, $R^1$, which is bonded in the bridging unit $C(R^1)_2$, is preferably selected, identically or differently on each occurrence, from the group consisting of H, D, F, a $C_{1-8}$-alkyl group and a mono- or polycyclic 5- to 20-membered aromatic or heteroaromatic ring system, where one of the $R^1$ may be linked to an L, forming a penta- or hexadentate ligand, where, in the case where two adjacent $R^1$ in each case form a mono- or polycyclic aromatic or heteroaromatic ring system, these two ring systems may be linked to one another by a single bond or a divalent unit G, where G is an —O—, —CH$_2$— or —C(CH$_3$)$_2$— unit, or two adjacent $R^1$ together form an oxo group, or two adjacent $R^1$ together form a divalent unit —O—(CH$_2$)$_m$—O— or —CH$_2$—(CH$_2$)$_m$—CH$_2$—, where m is equal to 1 or 2.

In accordance with the invention, the term "$C_{1-8}$-alkyl group" is intended to encompass all compounds which fall under the number-of-atoms subset of the term defined above as "$C_{1-40}$-alkyl group". The preferred groups falling thereunder are likewise preferred here.

In a further embodiment, $R^2$ is preferably selected, identically or differently on each occurrence, from the group consisting of a non-bonding electron pair, H, a $C_{1-6}$-alkyl group and a benzyl group.

In still a further embodiment, the substituents $R^1$ on Cy and Ar are selected from the group consisting of H, D, F, Cl, Br, I, CN and a $C_{1-10}$-alkyl group, in which one or more H atoms may be replaced by F. The substituents are furthermore preferably an aryl or heteroaryl group having 5 to 10 aromatic ring atoms, which may be substituted by one or more radicals $R^4$.

In accordance with the invention, the term "$C_{1-10}$-alkyl group" is intended to encompass all compounds which fall under the number-of-atoms subset of the term defined above as "$C_{1-40}$-alkyl group". The preferred groups falling thereunder are likewise preferred here.

In a further embodiment of the present invention, the compound of the formula I is preferably a compound of the following formula II:

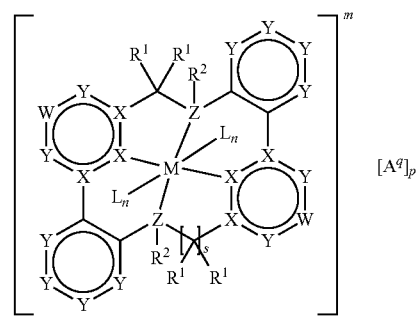

formula II where the symbols M, L, X, Z, A, $R^1$ and $R^2$ and the indices n, m, p, q and s have the same meanings as defined in the above embodiments, and the other symbols have the following meanings:

Y is, identically or differently on each occurrence, $CR^6$ or N; or precisely one Y per ring is $NR^6$, S or O if the group W in this ring stands for a bond;

W is, identically or differently on each occurrence, either not present, so that a covalent bond is formed between the two Y bonded to W, or is $CR^6$ or N, with the proviso that a maximum of two representatives from the unit formed from Y=W—Y can be nitrogen atoms;

$R^6$ is, identically or differently on each occurrence, selected from the group consisting of H, D, F, Cl, Br, I, CN, NO$_2$, a $C_{1-10}$-alkyl group, in which one or more H atoms may be replaced by F, a $C_{6-18}$-aryl group or $C_{1-18}$-heteroaryl group, each of which may carry one or more $C_{1-6}$-alkyl groups as substituents, a 5- to 18-membered heteroaryl group, a $C_{1-10}$-alkoxy group, a $C_{6-18}$-aryloxy group and a 5- to 18-membered heteroaryloxy group, or two $R^6$ in the vicinal position form a divalent group —$CR^7$=$CR^7$—$CR^7$=$CR^7$— with one another, or two $R^6$ in the vicinal position are linked to one another with formation of an aliphatic ring system;

$R^7$ is, identically or differently on each occurrence, selected from the group consisting of H, D, F, Cl, Br, I, CN, NO$_2$, a $C_{1-10}$-alkyl group, in which one or more H atoms may be replaced by F, a $C_{6-18}$-aryl group, which may carry a $C_{1-6}$-alkyl group as substituent, a 5- to 18-membered heteroaryl group, a $C_{1-10}$-alkoxy group, a $C_{6-18}$-aryloxy group and a 5- to 18-membered heteroaryloxy group, or two $R^7$ in the vicinal position form a divalent group —$CR^8$=$CR^8$—$CR^8$=$CR^8$— with one another;

$R^8$ is, identically or differently on each occurrence, selected from the group consisting of H, D, F, Cl, Br, I, CN, NO$_2$, a $C_{1-10}$-alkyl group, in which one or more H atoms may be replaced by F, a $C_{6-18}$-aryl group, which may carry a $C_{1-6}$-alkyl group as substituent, a 5- to 18-membered heteroaryl group, a $C_{1-10}$-alkoxy group, a $C_{6-18}$-aryloxy group and a 5- to 18-membered heteroaryloxy group.

In the formula II, the circle in each case stands for a 6π electron system, as generally usual in organic chemistry.

In accordance with the invention, the term "$C_{1-10}$-alkyl group, in which one or more H atoms may be replaced by F" is intended to encompass all compounds which fall under the number-of-atoms subset of the term defined above as "$C_{1-40}$-alkyl group". In addition, one or more of the H atoms may be replaced by F. Preferred groups here are methyl, i-propyl, i-butyl, t-butyl, t-pentyl, neopentyl and trifluoromethyl.

A $C_{6-18}$-aryl group, which may carry a $C_{1-6}$-alkyl group, is taken to mean all compounds which contain a monocyclic or polycyclic aromatic unit consisting of condensed rings, having 6 to 18 C atoms, which, in addition, may be substituted by one or more $C_{1-6}$-alkyl groups. Preferred examples are phenyl, 2,4,6-trimethylphenyl, o-, m- or p-tolyl, o-, m- or p-fluorophenyl, o-, m- or p-t-butylphenyl and 1- or 2-naphthyl.

A 5- to 18-membered heteroaryl group is taken to mean a heteroaromatic ring system having 5 to 18 ring atoms, as defined above.

In accordance with the invention, the term "$C_{1-10}$-alkoxy group" is intended to encompass all compounds which fall under the number-of-atoms subset of the term defined above as "$C_{1-40}$-alkoxy group". The preferred groups falling thereunder are likewise preferred here.

The term $C_{6-10}$-aryloxy group is intended to encompass aromatic compounds having 6 to 10 carbon atoms which are bonded via an O atom. Examples thereof are phenyloxy and naphthyloxy.

The aliphatic ring system has the same meaning as defined above.

In still a further embodiment of the present invention, the compound of the formula I is preferably a compound of the following formula III:

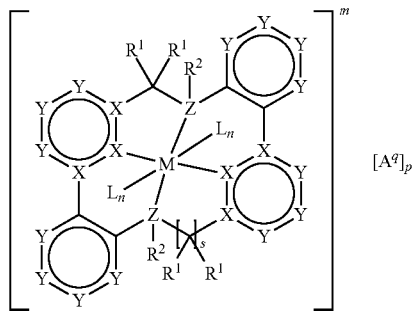

formula III where the symbols M, L, X, Y, Z, A, $R^1$ and $R^2$ and the indices n, m and q have the same meanings as defined above.

In a further embodiment, it is preferred for the compound of the formula III to be a compound in which X is a carbon atom and Y, identically or differently on each occurrence, is $CR^6$, where $R^6$ has the same meaning as defined above.

In still a further embodiment, it is preferred for the compound of the formula III to be a compound in which at least one representative of the two X is a nitrogen and the other is a carbon atom, and Y, identically or differently on each occurrence, is $CR^6$, where $R^6$ has the same meaning as defined above.

In still a further embodiment, it is preferred for the compound of the formula III to be a compound in which X is a carbon atom, and at least one representative from Y is a nitrogen atom and the other Y stand, identically or differently on each occurrence, for $CR^6$.

In still a further embodiment, it is preferred for a maximum of one group Y per ring to stand for N.

In formula III, two $R^6$ in the vicinal position can form a divalent group —$CR^7$=$CR^7$—$CR^7$=$CR^7$—, where $R^7$ has the same meaning as defined above, or two $R^6$ in the vicinal position can be linked to one another with formation of an aliphatic ring system having 4 to 10 carbon atoms, or at least one representative of the $R^6$ represents a group selected from H, D, F, CN, $CF_3$, Me, i-propyl, t-butyl, phenyl, 2,4,6-trimethylphenyl, phenyloxy and diphenylamine, and the other representatives represent a hydrogen atom or D.

In a particularly preferred embodiment, two radicals $R^6$ which are not bonded to the same aromatic unit are other than H, particularly preferably such that the compound according to the invention has a two-fold axis of rotation.

Particular preference is given to a compound of the formula III in which Y is in each case, identically or differently on each occurrence, N or CH, very particularly preferably CH.

In a further embodiment of the present invention, the compound of the formula I is preferably a compound of the following formula IV:

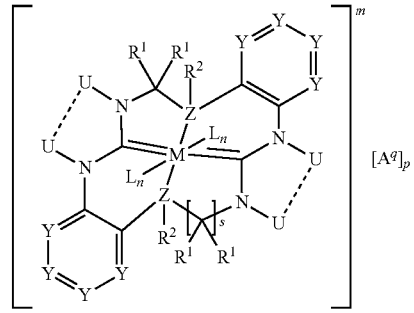

formula IV where the symbols M, L, Y, Z, A, $R^1$ and $R^2$ and the indices n, m, p and q have the same meanings as defined above, and the dashed lines represent either a single covalent bond or a double covalent bond, where, in the case where the dashed line represents a single covalent bond, U is in each case a $CH_2$ or $C(R^5)_2$ unit, and, in the case where the dashed line represents a double covalent bond, U is a $CR^6$ unit, where $R^5$ and $R^6$ are as defined above.

Two $R^5$ or $R^6$ in the vicinal position may together form a divalent group —CH=CH—CH=CH—.

In still a further embodiment of the present invention, the compound of the formula I is preferably a compound of the following formula V:

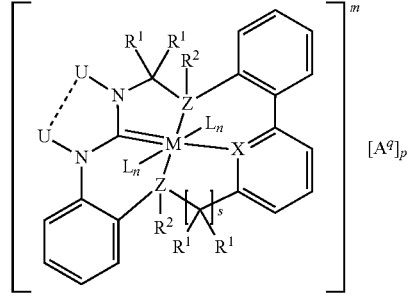

formula V where the symbols M, L, Z, X, A, $R^1$ and $R^2$ and the indices n, m and q have the same meanings as defined above, and U is equal to $CR^6$, where $R^6$ is as defined above.

Two $R^6$ in the vicinal position may preferably together form a divalent group —CH=CH—CH=CH—.

In a further embodiment of the present invention, it is preferred in the above-mentioned formulae I to III and V for X, which coordinates to the metal, to be equal to N, for Z to be equal to N, for $R^2$ to be a non-bonding electron pair, and for M to be equal to Pt, in particular Pt(II).

In a further embodiment of the present invention, it is preferred in the above-mentioned formulae I to III and V for X, which coordinates to the metal, to be equal to C and for M to be equal to Pt, in particular Pt(II).

In all embodiments of the present invention, the ligand L is preferably selected, identically or differently on each occurrence, from the group consisting of the following:

CO, NO, SH, OH, carbenes, such as, for example, Arduengo carbenes, isonitriles, such as, for example, tert-butyl isonitrile, cyclohexyl isonitrile, adamantyl isonitrile, phenyl isonitrile, mesityl isonitrile, 2,6-dimethylphenyl isonitrile, 2,6-diisopropylphenyl isonitrile, 2,6-di-tert-butylphenyl isonitrile, amines, such as, for example, trimethylamine, triethylamine, morpholine, phosphines, such as, for example, trifluorophosphine, trimethylphosphine, tricyclohexylphosphine, tri-tert-butylphosphine, triphenylphosphine, tris(pentafluorophenyl)phosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tert-butylstibine, triphenylstibine, tris(pentafluorophenyl)stibine, nitrogen-containing heterocycles, such as, for example, pyridine, pyridazine, pyrazine, pyrimidine, triazine, hydride, deuteride, the halides F, Cl, Br and I, alkylacetylides, such as, for example, methyl-C≡C—, tert-butyl-C≡C—, aryl- and heteroarylacetylides, such as, for example, phenyl-C≡C—, cyanide, cyanate, isocyanate, thiocyanate, isothiocyanate, aliphatic or aromatic alcoholates, such as, for example, methanolate, ethanolate, propanolate, isopropanolate, tert-butylate, phenolate, aliphatic or aromatic thioalcoholates, such as, for example, methanethiolate, ethanethiolate, propanethiolate, isopropanethiolate, tert-butanethiolate, thiophenolate, amides, such as, for example, dimethylamide, diethylamide, diisopropylamide, morpholide, carboxylates, such as, for example, acetate, trifluoroacetate, propionate, benzoate, and anionic, nitrogen-containing heterocycles, such as pyrrolide, imidazolide, pyrazolide. The alkyl groups in these groups are preferably $C_{1-20}$-alkyl groups, particularly preferably $C_{1-10}$-alkyl groups, very particularly preferably $C_{1-4}$-alkyl groups. An aryl group is preferably taken to mean $C_{6-18}$-aryl groups. The above definitions of these groups are also intended to apply here.

In a further preferred embodiment of the present invention, in each case one $R^1$ in the above-mentioned formulae I to V is linked to in each case one L, where a 5- or 6-dentate ligand is formed. Preferred units from —$R^1$-L are selected from the group consisting of the following:

—CH$_2$CH$_2$PMe$_2$, —CH$_2$CH$_2$PPh$_2$, —CH$_2$CH$_2$O$^-$, —CH$_2$CH$_2$S$^-$, —CH$_2$COO$^-$, —CH$_2$COS$^-$,

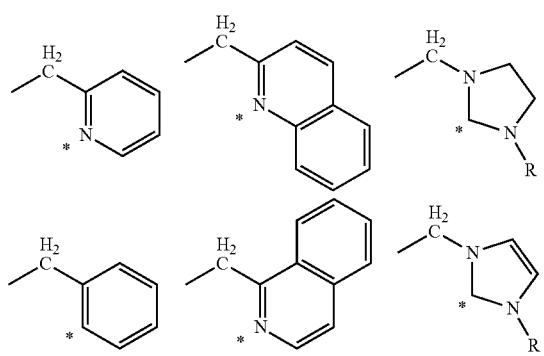

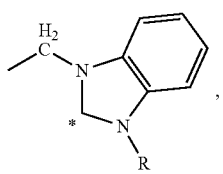

where the position denoted by * is coordinated to the metal.

Furthermore, it is a preferred embodiment that in each case one $R^1$ in the above-mentioned formulae I to V is linked to a ligand L and an opposite $R^2$. The linking of $R^1$ and $R^2$ preferably takes place in such a way that L is bonded to these two radicals. In this way, a penta- or hexadentate ligand is formed in the form of a cage. An example of a complex containing a hexadentate cage ligand is shown by the following formula VI:

formula VI

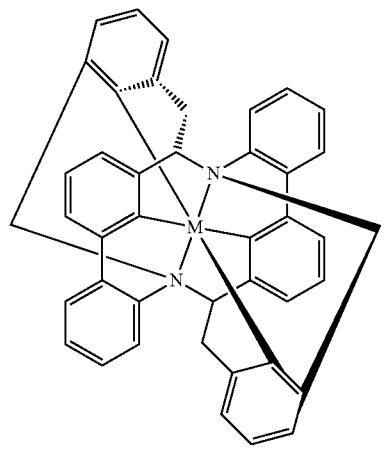

The complex of the formula VI should not be taken to have a restrictive meaning. The same radicals as described for the above-mentioned formulae I to V can be bonded to the corresponding positions of the ligand of the formula VI.

The compounds according to the invention can be positively charged, negatively charged or uncharged. They are particularly preferably charge-neutral, i.e. particularly preferably m=0 and the counterion A is not present, i.e. p=0.

In a further preferred embodiment of the invention, the index s=1. The ligand is thus preferably a macrocyclic ligand.

It is additionally preferred for the indices and radicals in the formulae I to V to be selected so that the compounds according to the invention have a centre of inversion or a two-fold axis of rotation.

In addition, it is advantageous for the dipole moment of the compounds according to the invention to be 3 debye or less, preferably 1 debye or less and particularly preferably 0.1 debye or less.

Besides the preferred compounds mentioned above, particular preference is furthermore given to the compounds shown in Table 1 below:

TABLE 1
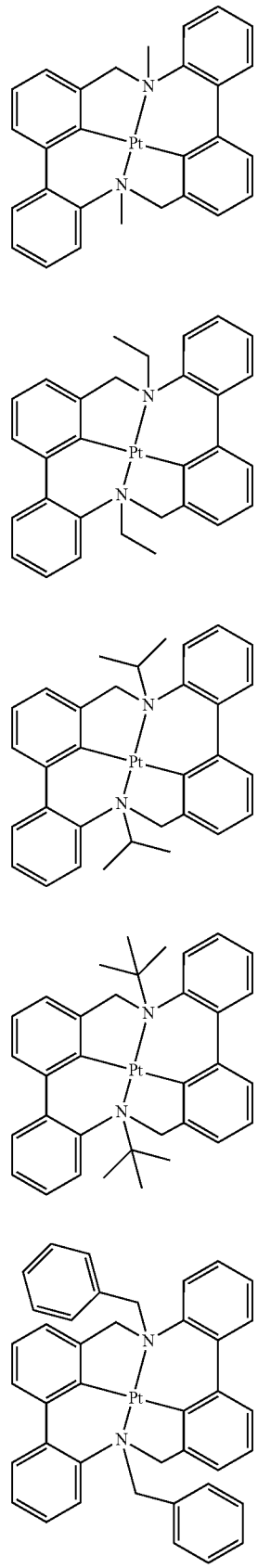
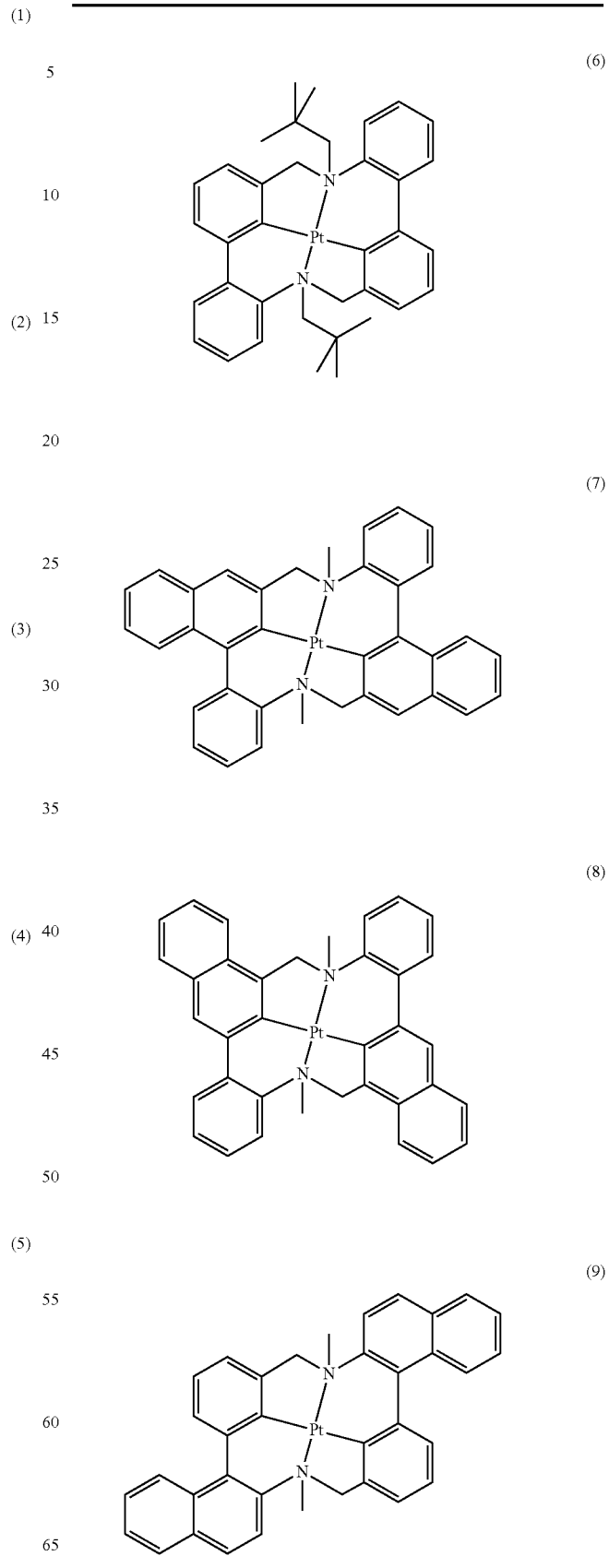

TABLE 1-continued
(10)
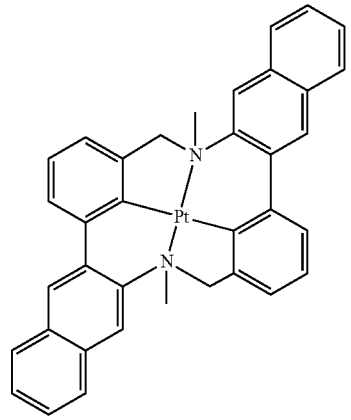
(11)
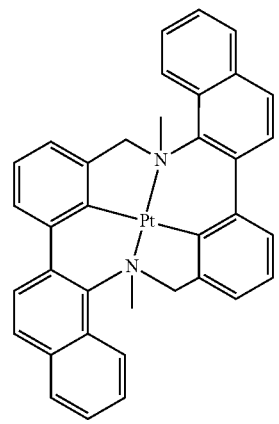
(12)
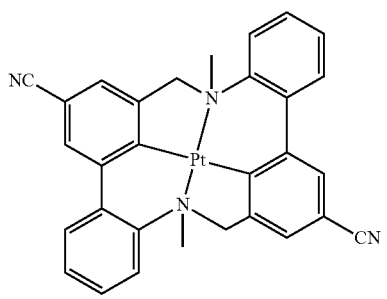
(13)
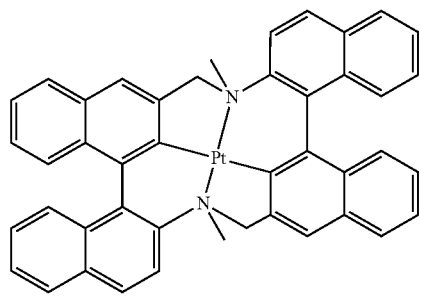
TABLE 1-continued
(14)
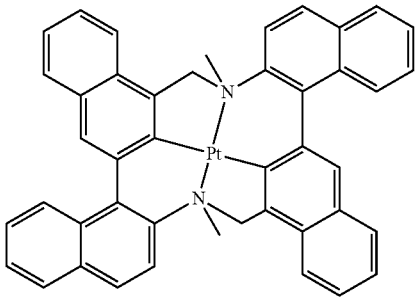
(15)
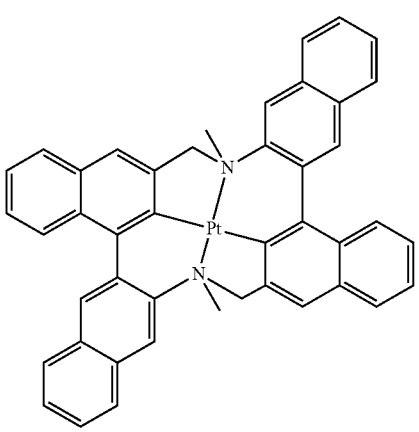
(16)
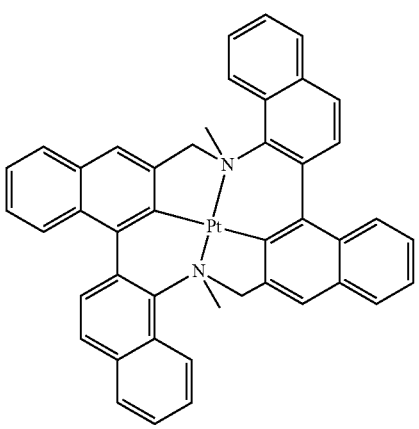
(17)
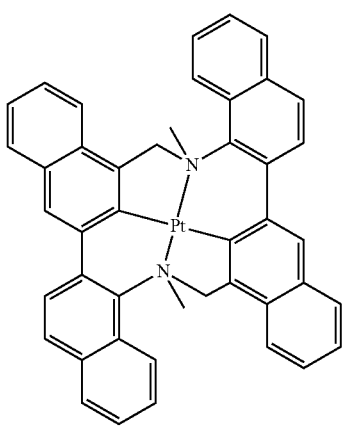

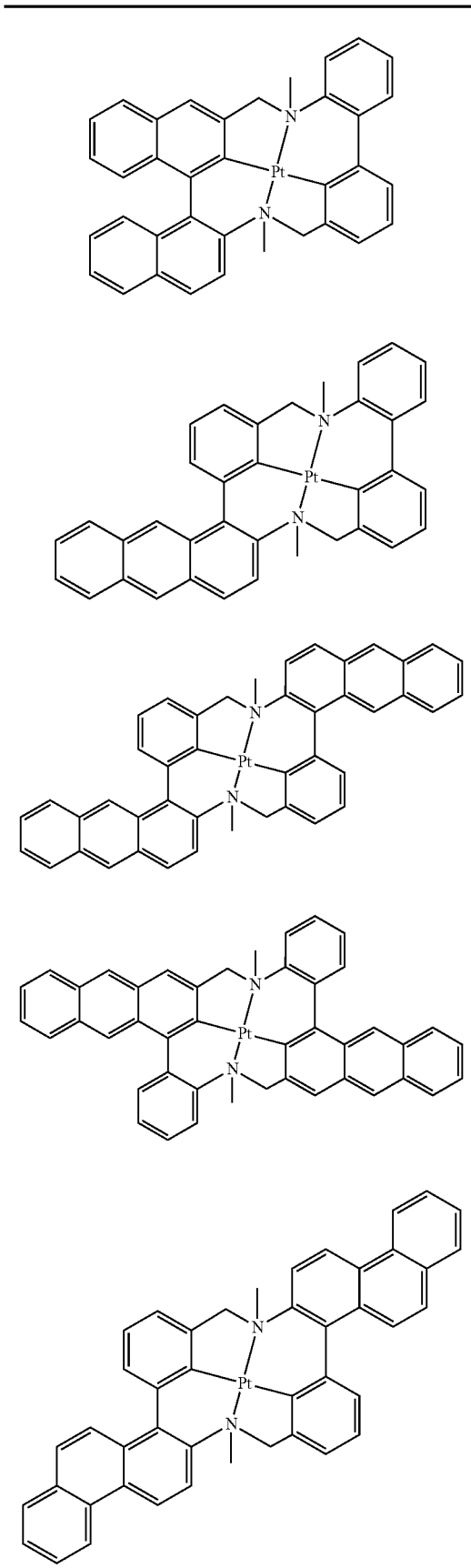

TABLE 1-continued
(27) 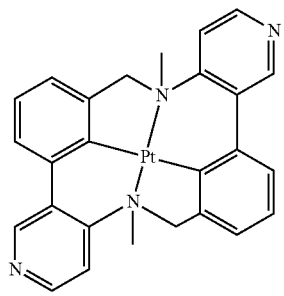
(28) 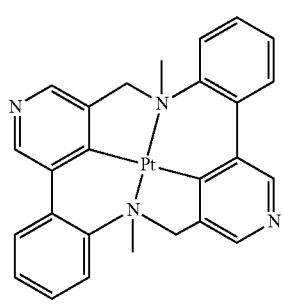
(29) 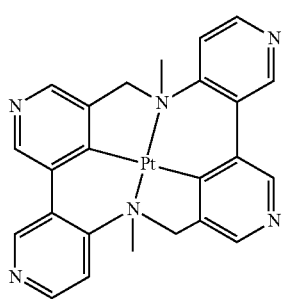
(30) 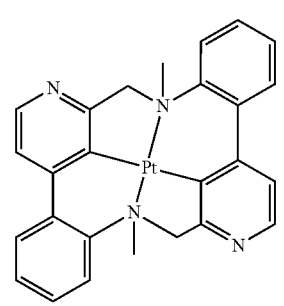
(31) 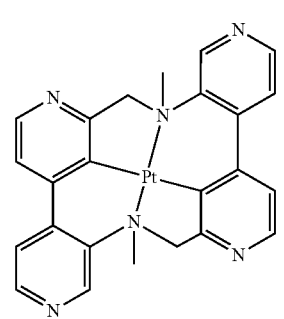
(32) 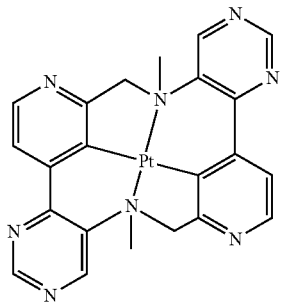
(33) 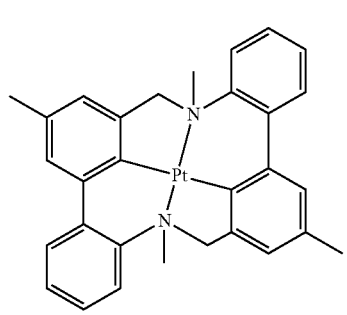
(34) 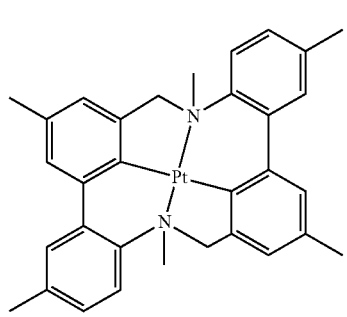
(35) 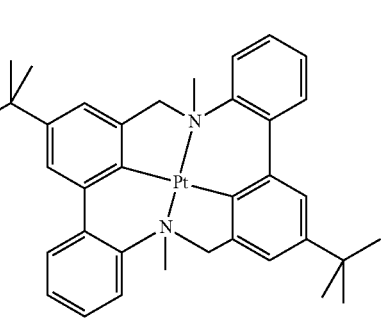
(36) 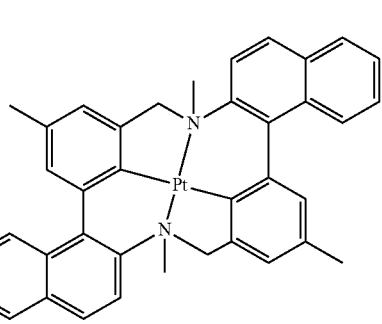

TABLE 1-continued
(37)
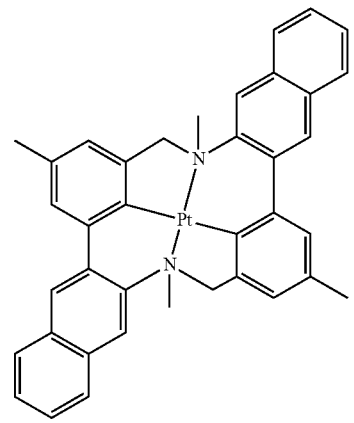
(38)
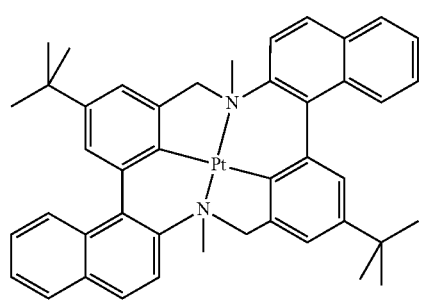
(39)
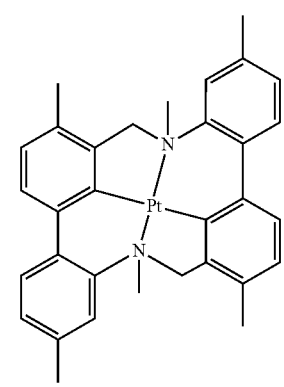
(40)
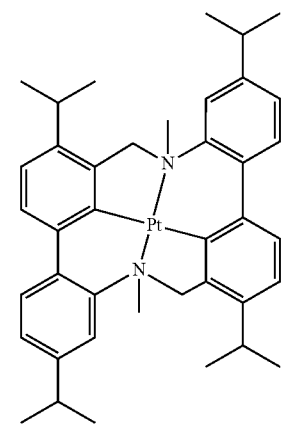
TABLE 1-continued
(41)
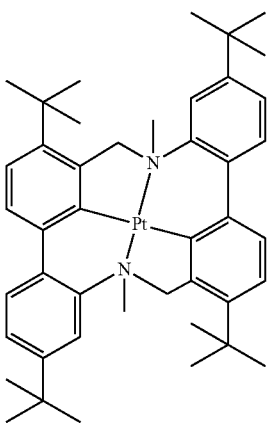
(42)
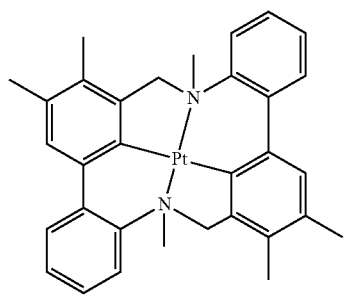
(43)
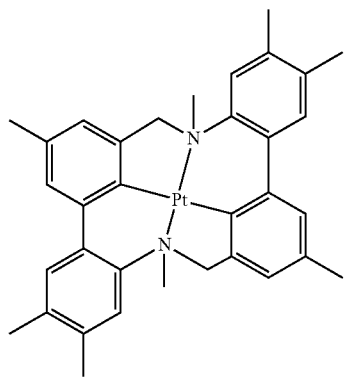
(44)
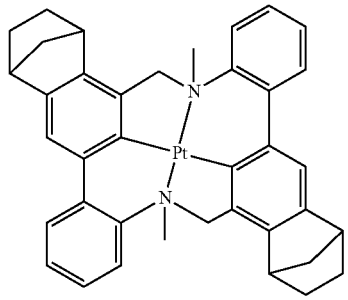

TABLE 1-continued
(45)
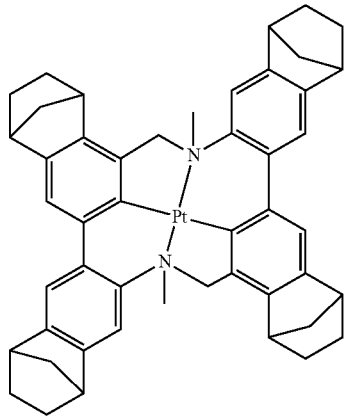
(46)
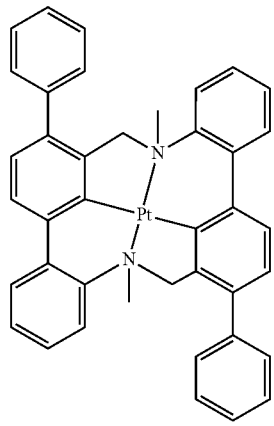
(47)
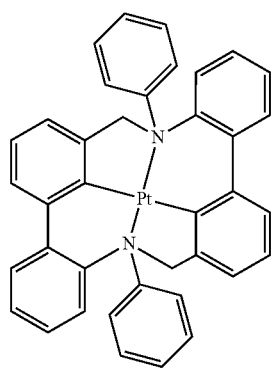
TABLE 1-continued
(48)
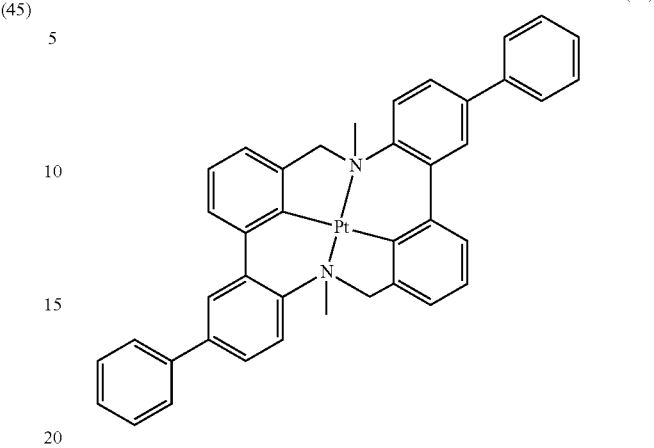
(49)
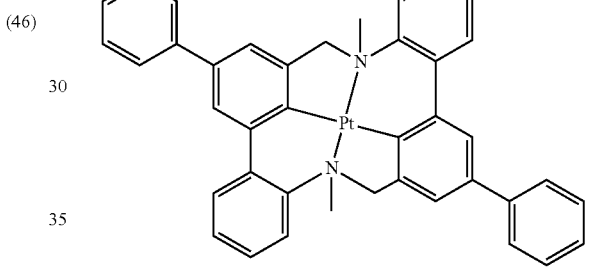
(50)
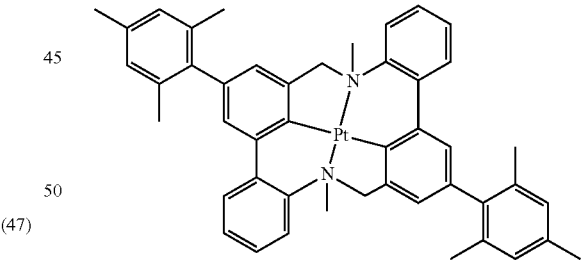
(51)
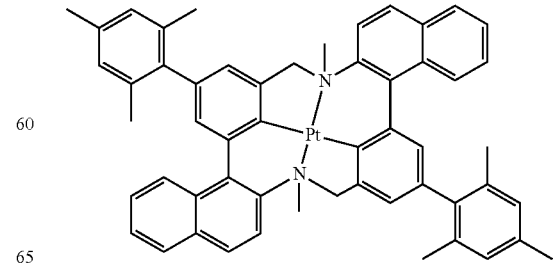

TABLE 1-continued
(52)
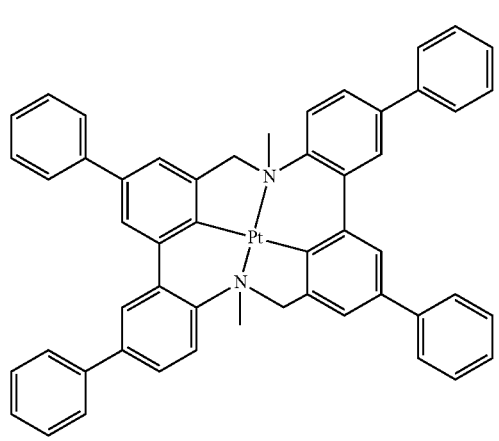
(53)
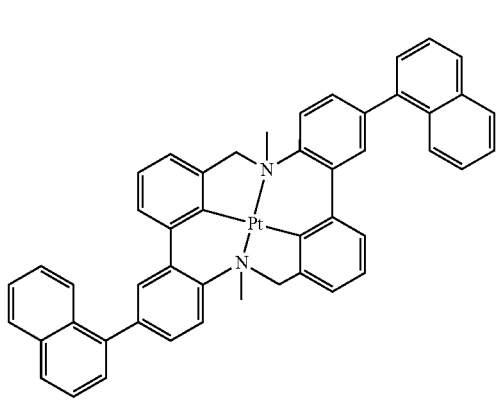
(54)
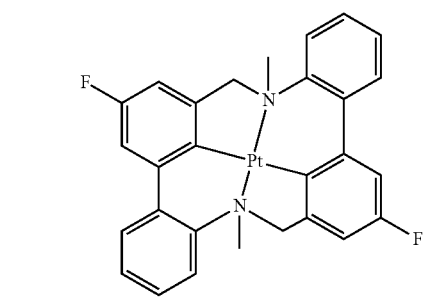
(55)
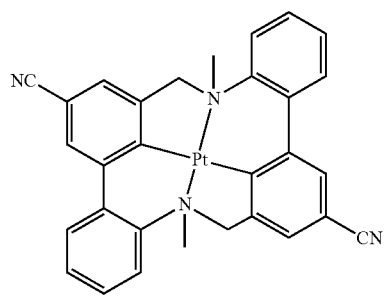
(56)
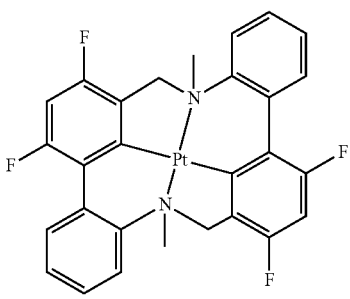
(57)
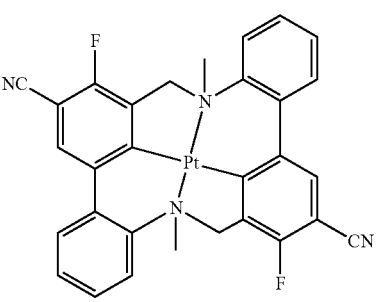
(58)
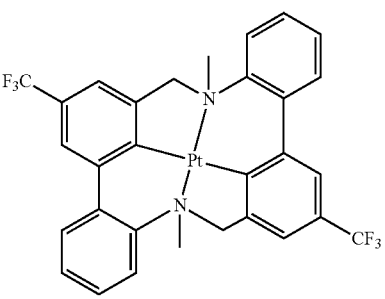
(59)
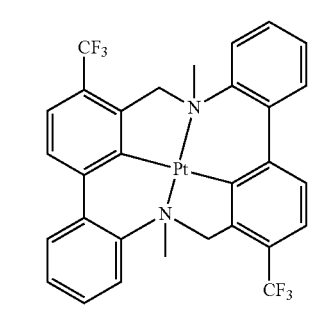

TABLE 1-continued
(60)
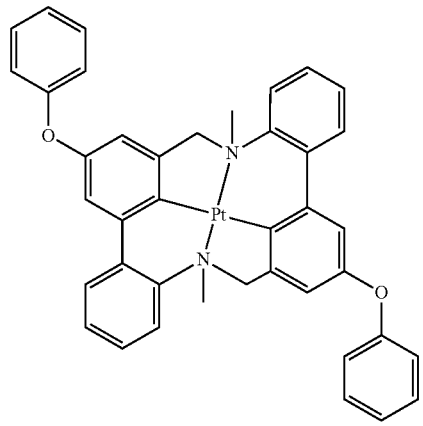
(61)
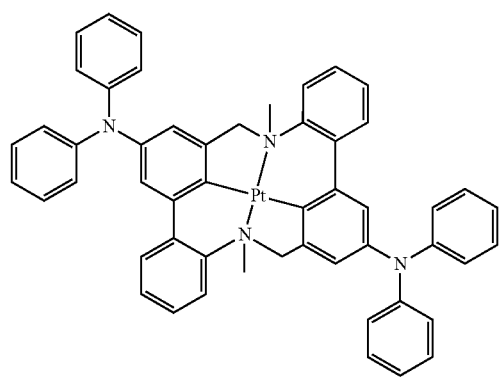
(62)
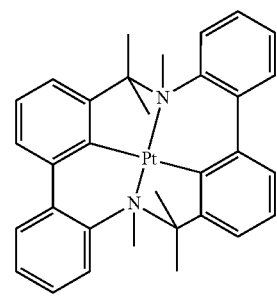
(63)
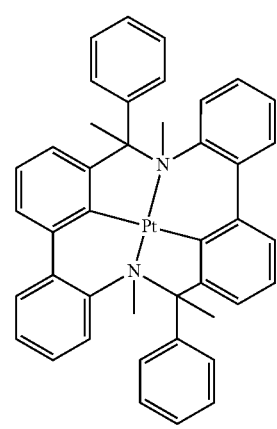
TABLE 1-continued
(64)
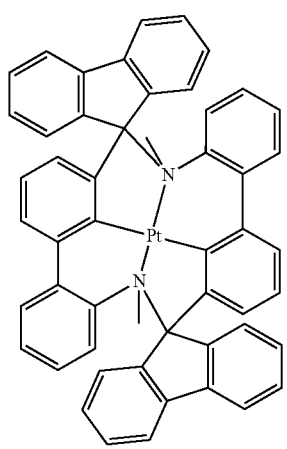
(65)
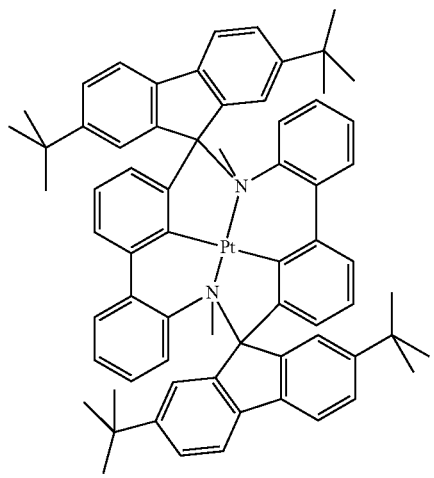
(66)
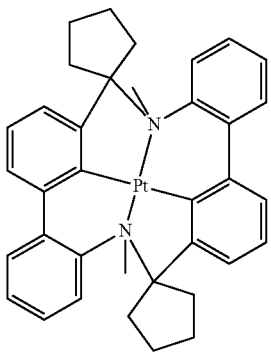

TABLE 1-continued
(67) 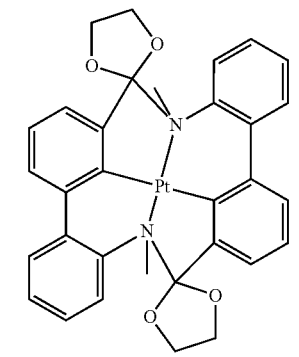
(68) 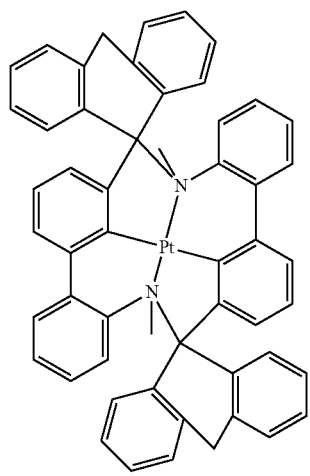
(69) 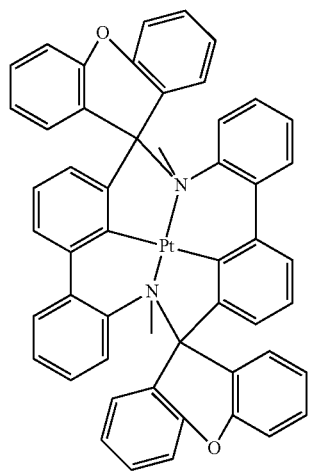
TABLE 1-continued
(70) 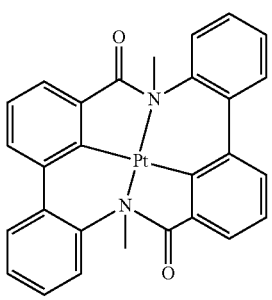
(71) 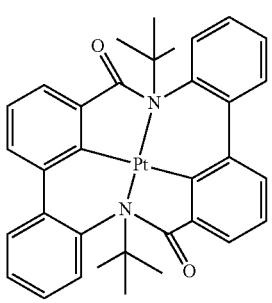
(72) 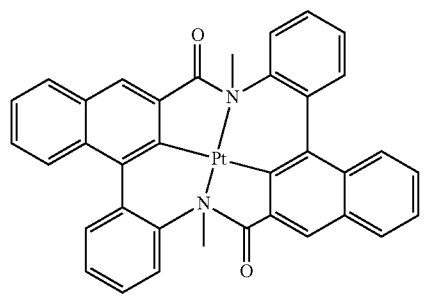
(73) 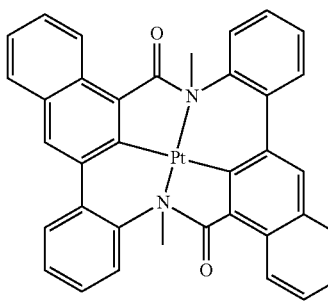
(74) 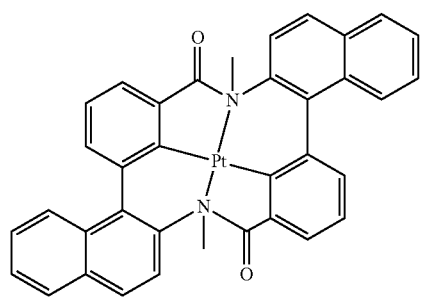

TABLE 1-continued
(75)
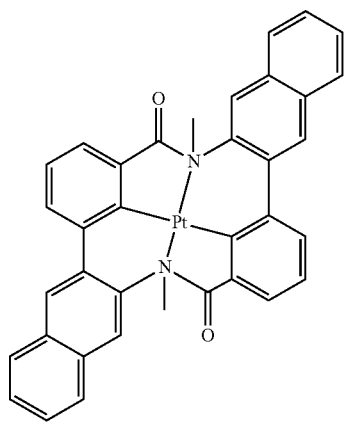
(76)
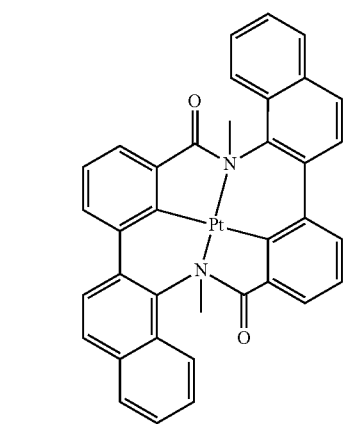
(77)
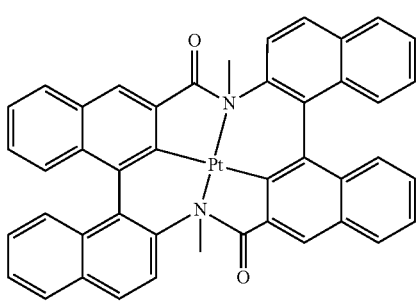
(78)
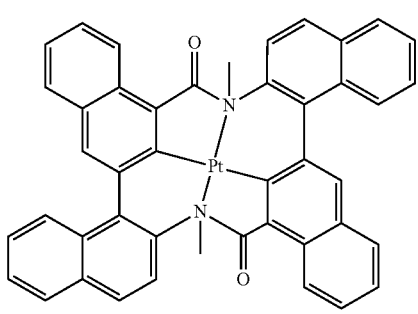
TABLE 1-continued
(79)
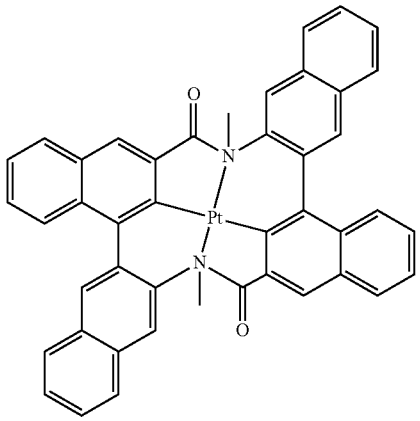
(80)
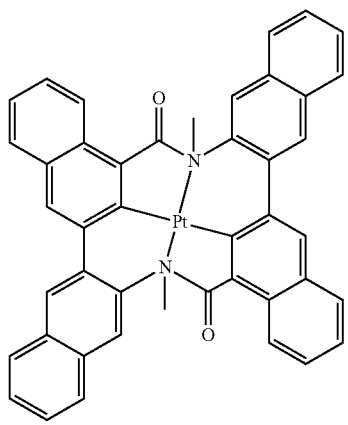
(81)
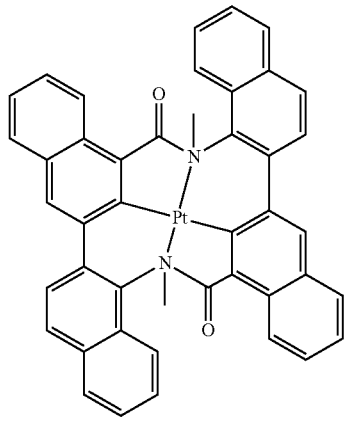
(82)
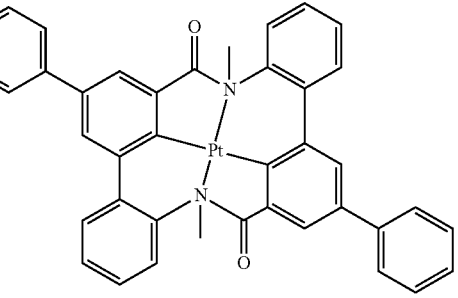

TABLE 1-continued
(83)
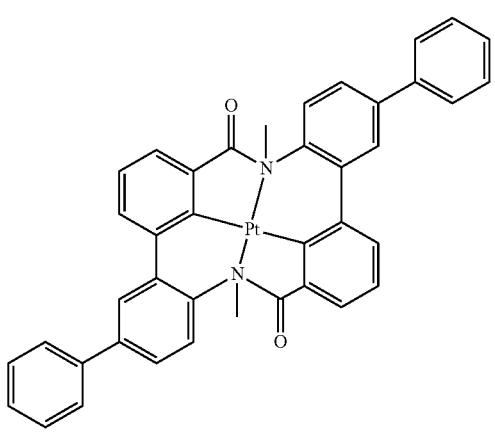
(87)
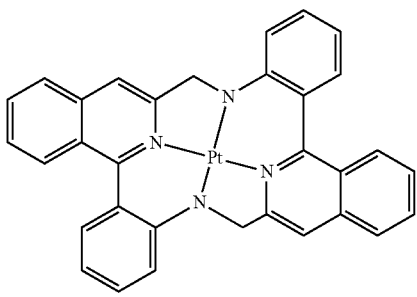
(84)
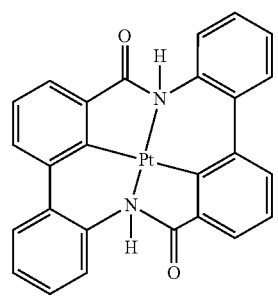
(88)
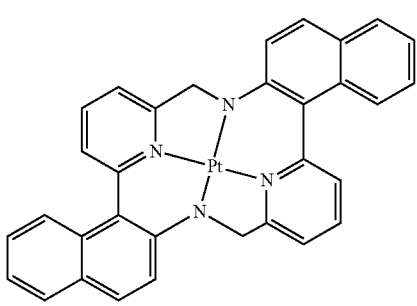
(85)
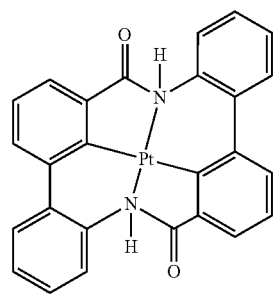
(89)
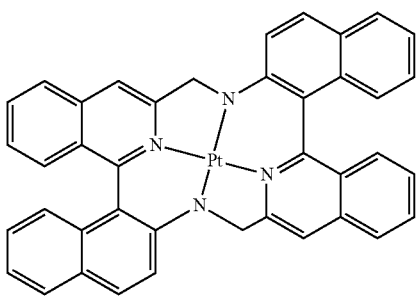
(86)
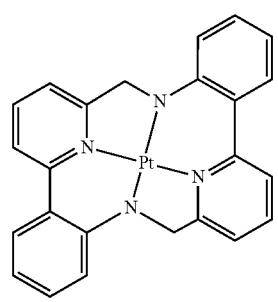
(90)
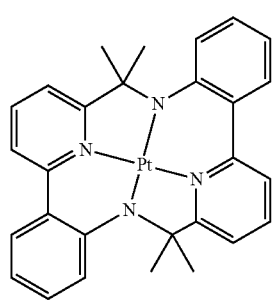

TABLE 1-continued
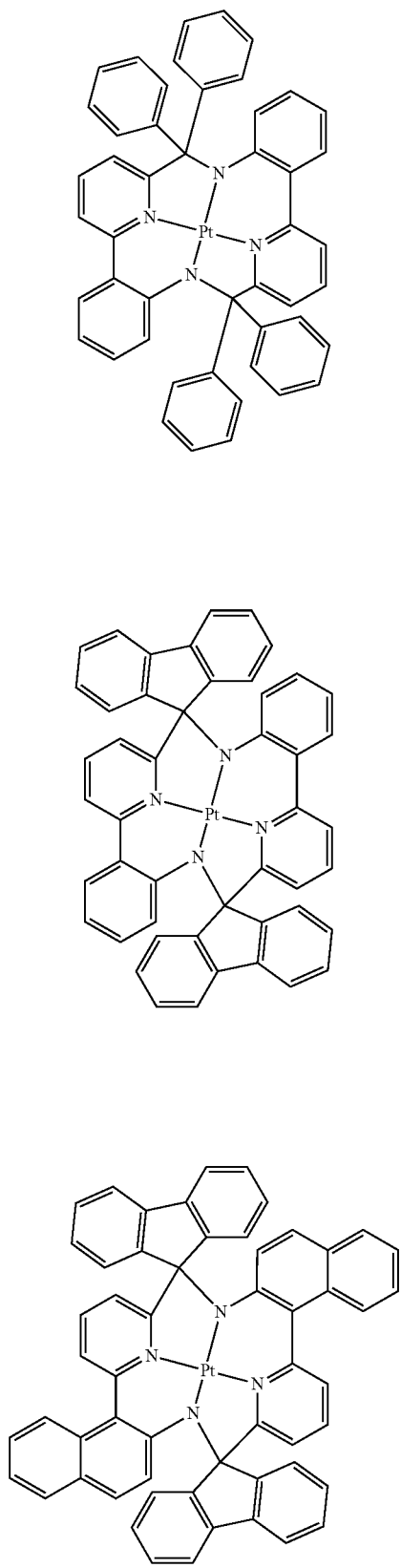
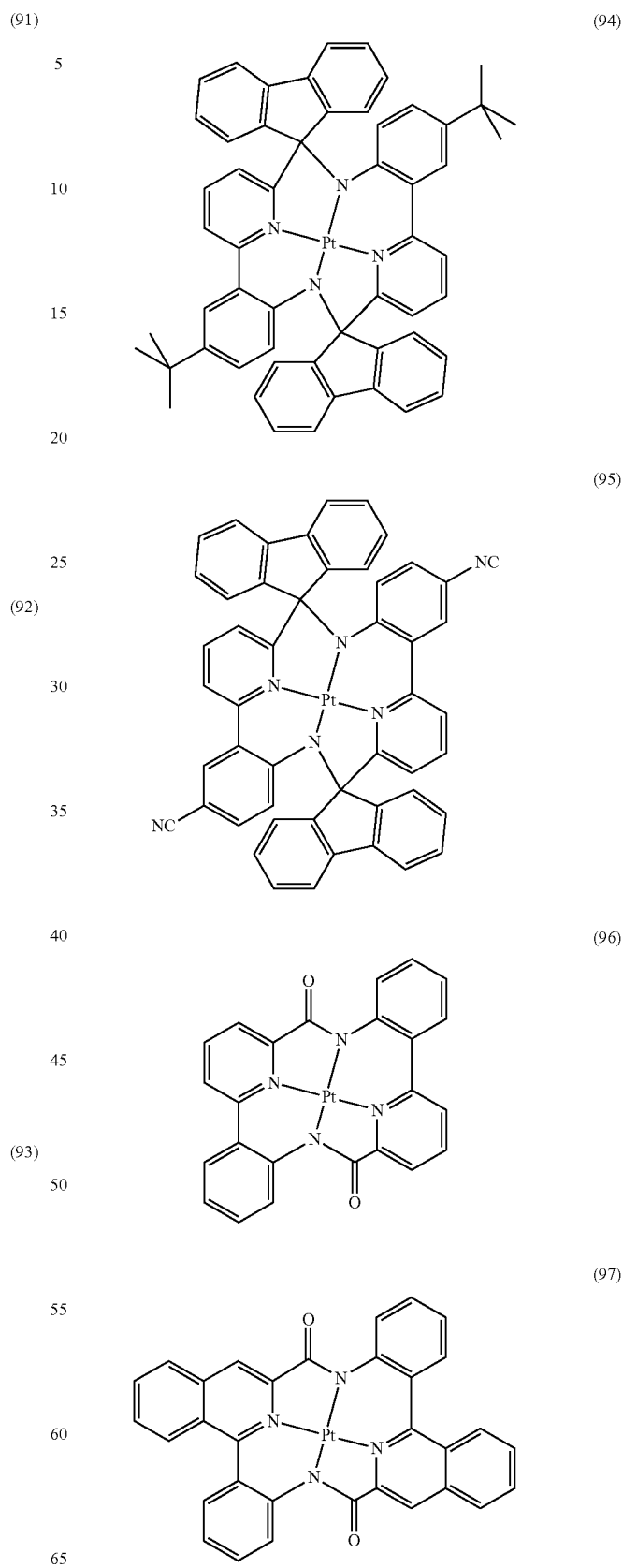

TABLE 1-continued
(98)
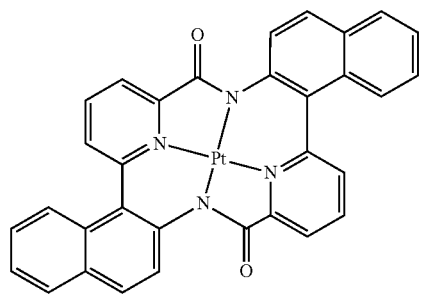
(99)
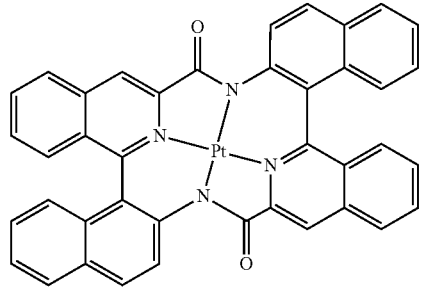
(100)
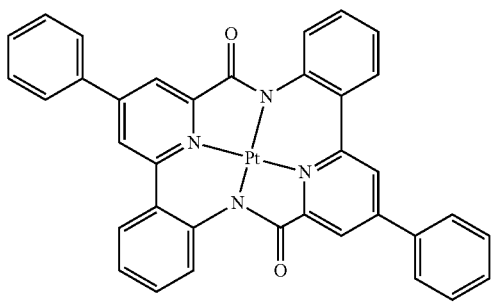
(101)
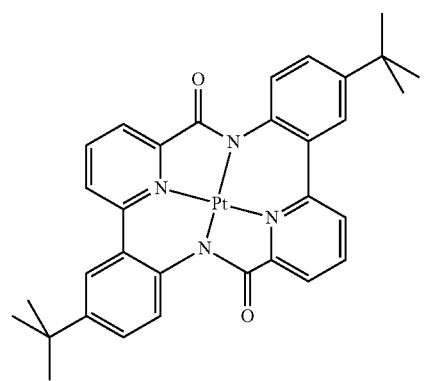
TABLE 1-continued
(102)
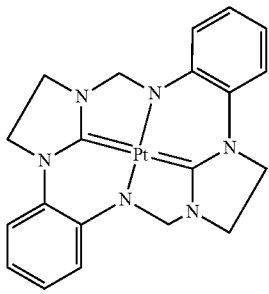
(103)
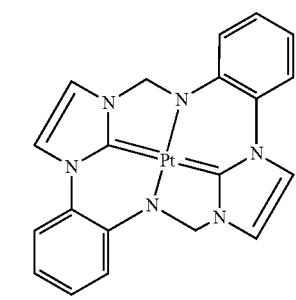
(104)
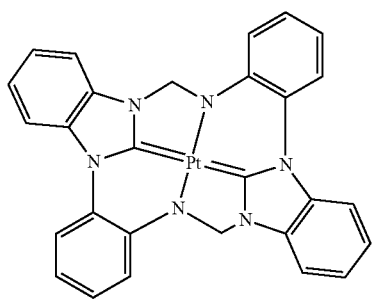
(105)
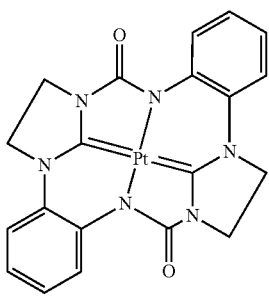
(106)
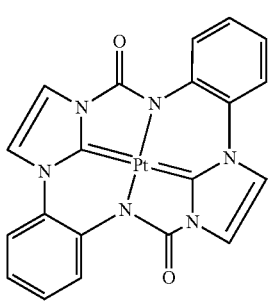

TABLE 1-continued
(107)
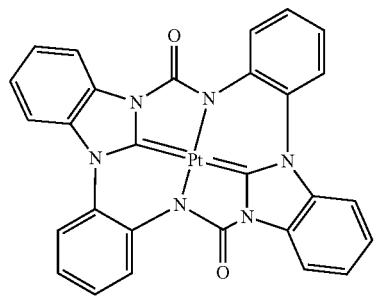
(108)
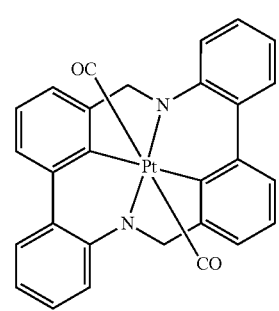
(109)
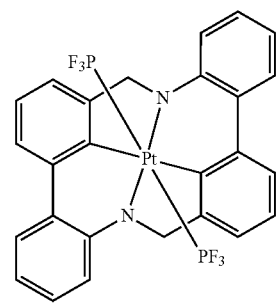
(110)
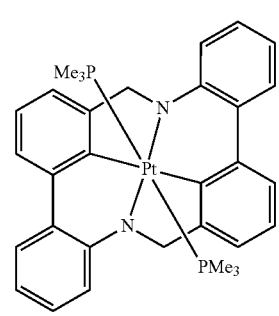
(111)
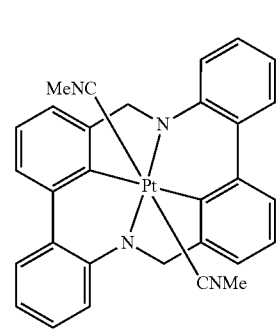
(112)
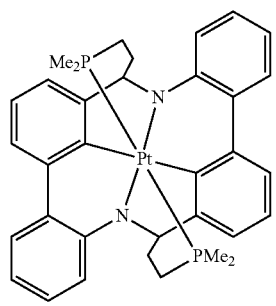
(113)
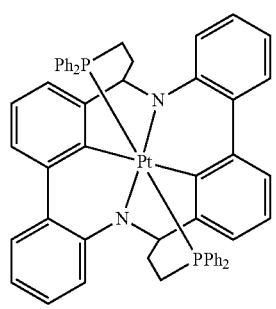
(114)
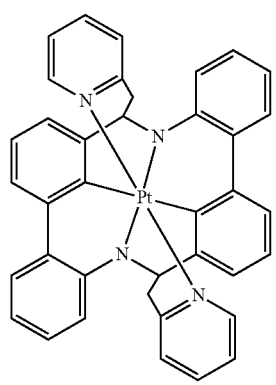
(115)
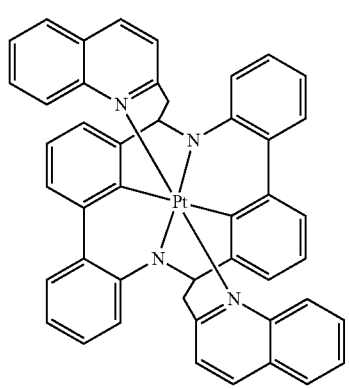

TABLE 1-continued
(116)
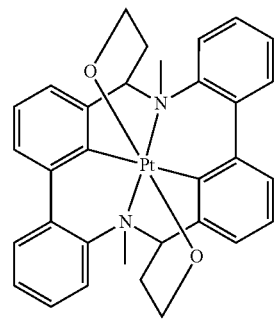
(117)
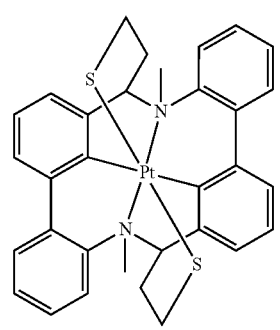
(118)
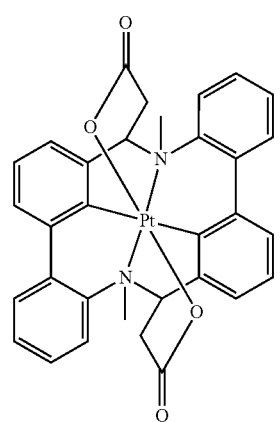
(119)
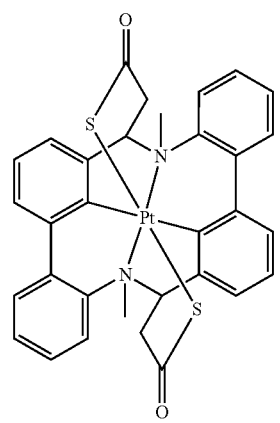
TABLE 1-continued
(120)
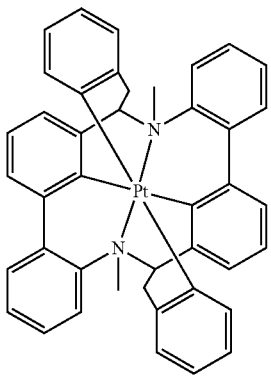
(121)
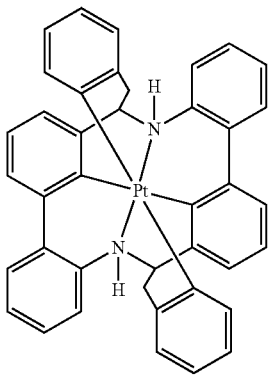
(122)
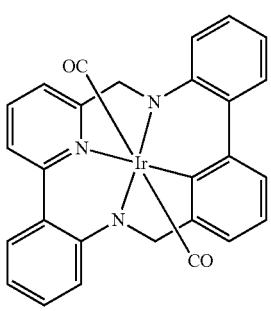
(123)
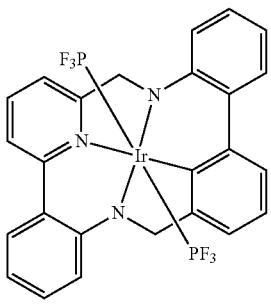

TABLE 1-continued
(124)
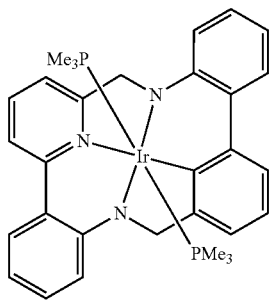
(125)
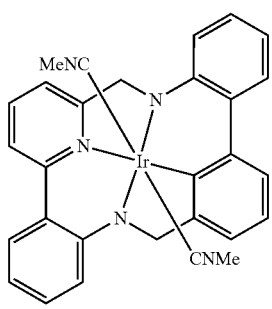
(126)
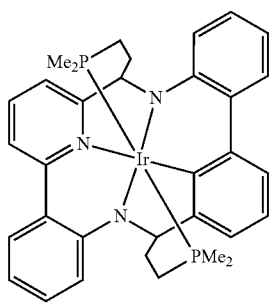
(127)
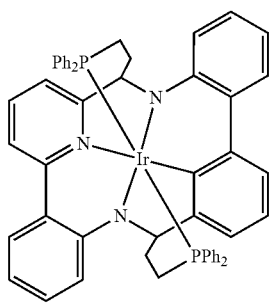
(128)
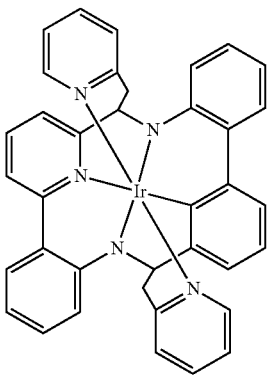
(129)
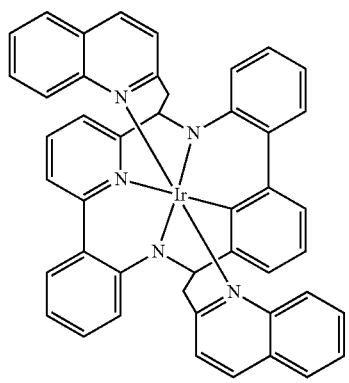
(130)
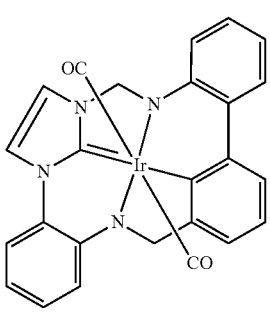
(131)
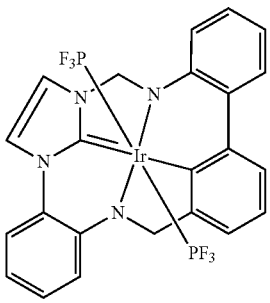

TABLE 1-continued (132)
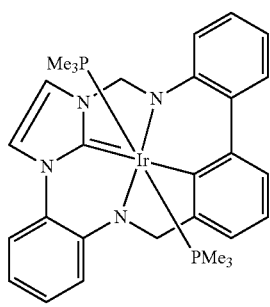

(133)
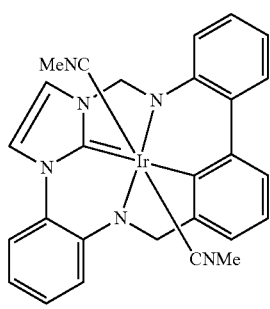

(134)
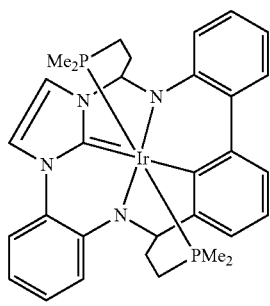

(135)
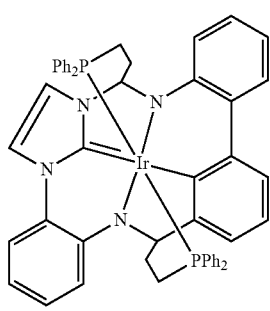

TABLE 1-continued (136)
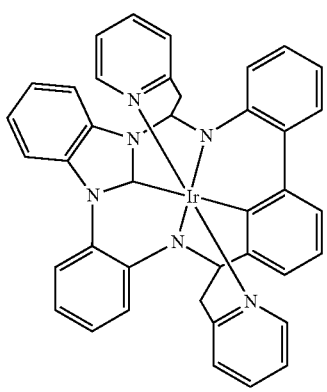

(137)
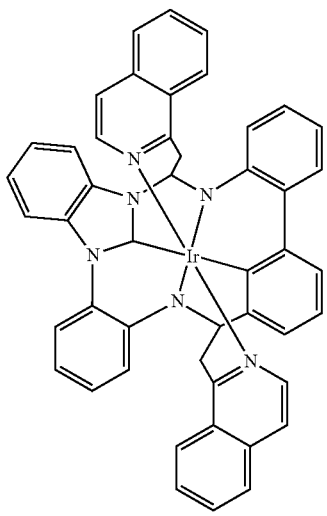

The present invention also relates to a ligand of the general formula Ia:

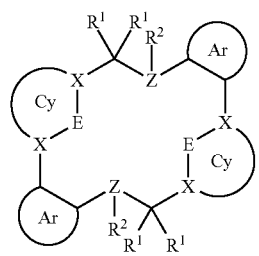

formula Ia where the symbols and indices used have the same meanings as defined above in the description of the compounds according to the invention, and E stands, identically or differently on each occurrence, for CH or N.

In a further embodiment, the ligand of the formula Ia is preferably a ligand of the following formula IIa:

formula IIa

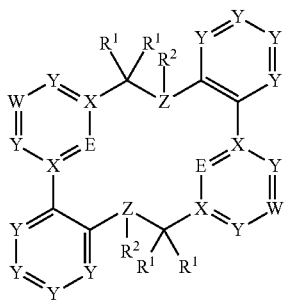

where the symbols and indices used have the same meanings as defined above in the description of the compounds according to the invention, and E has the meaning indicated above.

In still a further embodiment of the present invention, the ligand of the formula IIa is preferably a ligand of the following formula IIIa:

formula IIIa

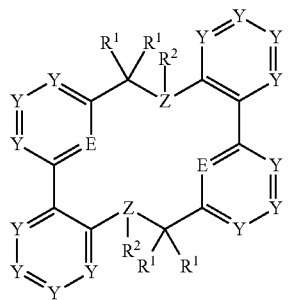

where the symbols and indices used have the same meanings as defined above in the description of the compounds according to the invention, and E has the meaning indicated above.

In still a further embodiment of the present invention, the ligand of the formula IIa is preferably a ligand of the following formula IVa:

formula IVa

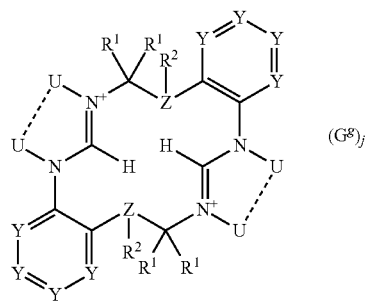

where the symbols and indices used have the same meanings as defined above in the description of the compounds according to the invention, and G is any desired anion having the charge g, where g is equal to −1 or −2 and j is equal to 1 or 2. The compound of the formula IVa is outwardly neutral.

Examples of these anions are bromide, iodide, $PF_6^-$, $BF_4^-$, sulfate and oxalate.

In still a further embodiment of the present invention, the ligand of the formula IIa is preferably a ligand of the following formula Va:

formula Va

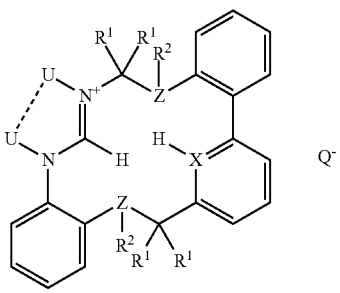

where the symbols and indices used have the same meanings as defined above in the description of the compounds according to the invention, and $Q^-$ is any desired anion.

Preferred anions are bromide, iodide, $PF_6^-$ and $BF_4^-$.

The present invention also relates to the use of a ligand of the formula Ia to Va for the preparation of a metal complex. Particularly preferred metal complexes here are the compounds of the formula I to V according to the invention.

The invention also relates to a process for the preparation of a compound of the general formula I to V.

The ligand synthesis can be carried out, for example, as depicted in general terms below in Scheme 1 by cyclocondensation (step 1) of two identical or different ligand precursors, which are provided with suitable leaving groups Y. Examples of the leaving groups Y are the following: OH, $NH_2$, $NH_3^+$, OTos, OMes, triflate, Cl, Br, I, carboxylate, etc. To this end, condensation reagents, for example water- or acid-binding assistants, or also catalysts can be added. The isomers arising on use of different ligand precursors can be separated by common procedures, such as fractional recrystallisation or chromatography. In a second step (step 2), the radicals $R^2$ can then optionally be introduced onto Z. This can be carried out by nucleophilic substitution (for example via alkylation), salt metathesis or by coupling reactions (for example Hartwig-Buchwald reaction) or others.

Scheme 1:

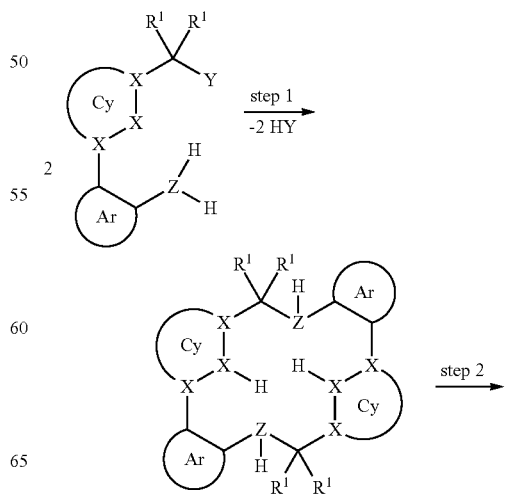

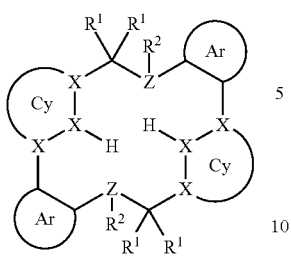

In order to illustrate the general Synthetic Scheme 1, two specific examples are shown below in Schemes 2 and 3.

Scheme 2: Synthesis of cyclic amide ligands:

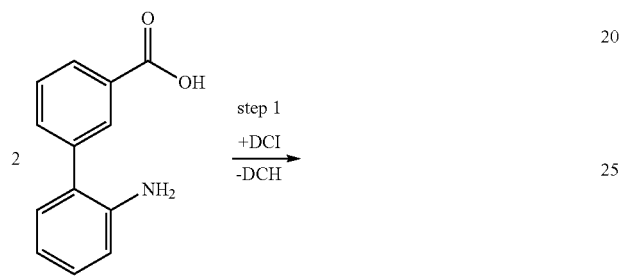

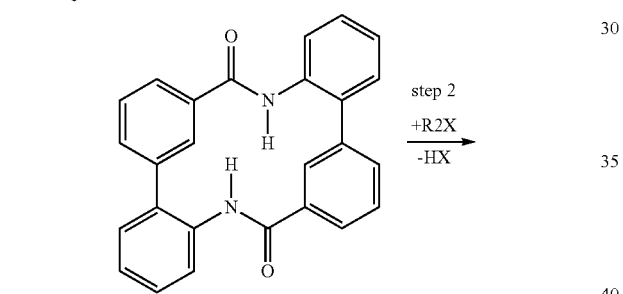

DCI = dicyclohexylcarbodiimide
DCH = dicyclohexylurea

Scheme 3: Synthesis of cyclic amine ligands:

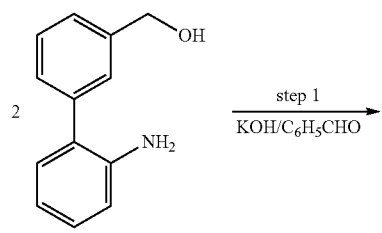

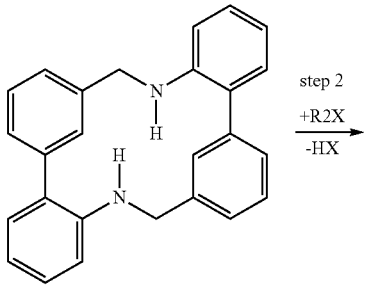

A general synthetic procedure for the preparation of metal complexes of the formula I, II, III, IV or V is depicted in methods A and B, which are shown in Schemes 4 and 5 below. The reaction of the cyclic ligand with a corresponding metal compound, which is usually employed as a solution of a suitable metal salt, for example $K_2PtCl_4$, $K_2PdCl_4$, $Pt(DMSO)_2Cl_2$, $IrCl_3$, $Ir(acac)_3$, $Na[Ir(acac)_2Cl_2]$, $AuCl_3$, or in the form of an organometallic precursor or complex compound, for example $Pt(CH_3)_2Cl_2$, $Pt(PPh_3)_4$, $Pt(dmso)_2Me_2$, $Ir(PPh_3)_2(CO)Cl$, $[Ir(COD)Cl]_2$ or $Ir(COD)_2BF_4$, results in the metal compounds according to the invention. The reaction can be carried out in the presence of acids (hydrohalic acids, phosphoric acid, organocarboxylic acids, etc.) or bases (organocarboxylates, carbonates, phosphates, alcoholates, alkoxides, etc.). Lewis acids (aluminium halides, silver salts, etc.) are optionally added in order to activate the ortho-metallation.

Scheme 4: Method A

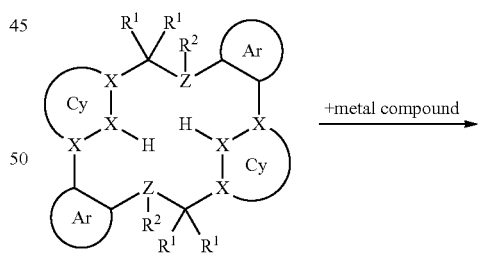

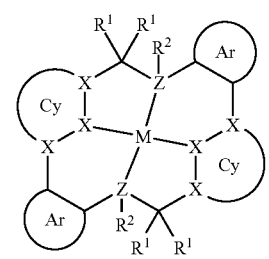

Besides the method shown in Scheme 4, the metal complexes can also be prepared in one step by a second method B in a template synthesis, starting from ligand precursors in the presence of a metal compound. This method B is shown in Scheme 5 below. In the template synthesis, firstly one or both ligand precursors coordinate to the metal compound, and in a second step, the cyclisation then takes place with removal of suitable leaving groups Y. The ortho-metallated metal complexes 1 formed as intermediates can either be isolated and then reacted further, or the reaction is carried out without isolation as far as the metal complexes according to the invention.

Scheme 5: Method B

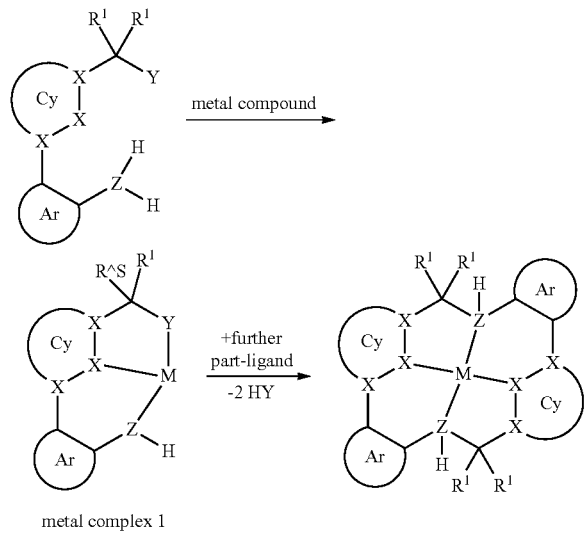

metal complex 1

Method B enables asymmetrical metal complexes according to the invention, consisting of two different ligand precursors, to be obtained specifically without it being necessary to use the separation methods described above.

The invention also relates to the use of the compounds according to the invention in an electronic device, in particular as emitting compound. The electronic device used in accordance with the invention can be organic electroluminescent devices (OLEDs) or polymeric electroluminescent devices (PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), but in particular organic electroluminescent devices (OLEDs, PLEDs).

The invention also relates to the use of the compounds according to the invention as charge-transport material and/or charge-injection material, preferably in a corresponding layer. This can be either a hole-transport layer, hole-injection layer, electron-transport layer or electron-injection layer. The use as charge-blocking material is also possible.

The invention likewise relates to electronic devices, such as, for example, organic electroluminescent devices or polymeric electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), but in particular organic electroluminescent devices (=organic light-emitting diodes, OLEDs, PLEDs), comprising one or more compounds of the formula I, II, III, IV or V, as defined above. The organic electronic device here comprises an anode, a cathode and at least one layer which comprises at least one organic or organometallic compound. However, the device may also comprise inorganic materials.

The compound of the formula I, II, III, IV or V is preferably within one layer in the electronic device.

The invention thus also relates to a layer comprising a compound of the formula I, II, III, IV or V, as defined above.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, charge-generation layers and/or organic or inorganic p/n junctions. It is likewise possible for an interlayer, which has, for example, an exciton-blocking function, to be introduced between two emitting layers. However, it should be pointed out that each of these layers does not necessarily have to be present. These layers may comprise compounds of the general formula I, II, III, IV or V, as defined above.

In a preferred embodiment of the invention, the compound of the formula I, II, III, IV or V is employed as emitting compound in an emitting layer or as charge-transport compound in a charge-transport layer. The organic electroluminescent device here may comprise one emitting layer or a plurality of emitting layers, where at least one emitting layer comprises at least one compound of the formula I, II, III, IV or V, as defined above. If a plurality of emission layers are present, these preferably have in total a plurality of emission maxima between 380 nm and 750 nm, resulting over-all in white emission, where white emission is characterised by CIE colour coordinates in the range from 0.28/0.29 to 0.45/0.41, i.e. various emitting compounds which are able to fluoresce or phosphoresce are used in the emitting layers. Particular preference is given to three-layer systems, where the three layers exhibit blue, green and orange or red emission (for the basic structure see, for example, WO 05/011013). The device may also be a hybrid white OLED which comprises both fluorescent and phosphorescent emitters.

If the compound of the formula I, II, III, IV or V is employed as emitting compound in an emitting layer, it is preferably employed in combination with one or more matrix materials. The mixture of the compound of the formula I, II, III, IV or V and the matrix material comprises between 1 and 99% by vol., preferably between 2 and 90% by vol., particularly preferably between 3 and 40% by vol., especially preferably between 5 and 15% by vol., of the compound of the formula I, II, III, IV or V, based on the entire mixture comprising emitter and matrix material. Correspondingly, the mixture comprises between 99 and 1% by vol., preferably between 98 and 10% by vol., particularly preferably between 97 and 60% by vol., especially preferably between 95 and 85% by vol., of the matrix material, based on the entire mixture comprising emitter and matrix material.

Preferred matrix materials are carbazole derivatives (for example CBP (N,N-biscarbazolylbiphenyl), mCBP or compounds in accordance with WO 05/039246, US 2005/0069729, JP 2004/288381, EP 1205527 or WO 08/086851), triarylamines, azacarbazoles (for example in accordance with EP 1617710, EP 1617711, EP 1731584, JP 2005/347160), indolocarbazole derivatives, for example in accordance with WO 07/063754 or WO 08/056746, ketones (for example in accordance with WO 04/093207 or in accordance with the unpublished application DE 102008033943.1), phosphine oxides, sulfoxides and sulfones (for example in accordance with WO 05/003253), oligophenylenes, aromatic amines (for example in accordance with US 2005/0069729), bipolar matrix materials (for example in accordance with WO 07/137725), silanes (for example in accordance with WO 05/111172), azaboroles or boronic esters, for example in accordance with WO 06/117052, triazine derivatives, for example in accordance with the unpublished application DE 102008036982.9, WO 07/063754 or WO 08/056746, zinc complexes (for example in accordance with WO 09/062578), aluminium complexes (for example BAlq) or diazasilole and tetraazasilole derivatives, for example in accordance with the unpublished application DE 102008056688.8.

Preference is furthermore given to an organic electroluminescent device in which one or more layers are applied by means of a sublimation process, in which the materials are vapour-deposited in vacuum sublimation units at an initial pressure below $10^{-5}$ mbar, preferably below $10^{-6}$ mbar. However, it is also possible for the initial pressure to be even lower, for example below $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), ink-jet printing or nozzle printing. Soluble compounds, which are obtained, for example, by suitable substitution, are necessary for this purpose. These processes are also particularly suitable for the processing of polymers.

These processes are generally known to the person skilled in the art and can be applied by him without problems to organic electroluminescent devices comprising compounds of the formula I, II, III, IV or V, as defined above.

Also possible are hybrid processes, in which one or more layers are applied from solution and one or more other layers are applied by vapour deposition.

The compounds according to the invention described above, in particular compounds which are substituted or functionalised by reactive groups, can be used as monomers for the preparation of corresponding oligomers, dendrimers or polymers.

The invention therefore furthermore relates to oligomers, polymers or dendrimers comprising one or more compounds of the formula I, II, III, IV or V, as defined above, where one or more bonds are present from the compounds of the formula I, II, III, IV or V to the polymer, oligomer or dendrimer. Depending on the linking of the compound of the formula I, II, III, IV or V, the complex therefore forms a side chain of the oligomer or polymer or is linked in the main chain. The polymers, oligomers or dendrimers may be conjugated, partially conjugated or non-conjugated. The oligomers or polymers may be linear, branched or dendritic.

For the preparation of the oligomers or polymers, the functionalised compounds of the formula I, II, III, IV or V are homopolymerised or copolymerised with further monomers. Preference is given to copolymers, where the compounds of the formula I, II, III, IV or V are preferably present to the extent of 0.01 to 50 mol %, particularly preferably in the range from 0.1 to 20 mol %. Suitable and preferred comonomers which form the polymer backbone are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or WO 07/017066) or also a plurality of these units. The proportion of these units in total is preferably in the region of at least 50 mol %. The polymers, oligomers and dendrimers may also contain further units, for example hole-transport units, in particular those based on triarylamines, and/or electron-transport units.

Polymers of this type comprising compounds of the general formula I, II, III, IV or V can be used for the production of PLEDs, in particular as emitter layer in PLEDs. A polymeric emitter layer can be produced, for example, by coating from solution (spin coating or printing processes).

The present invention therefore furthermore relates to a solution or formulation comprising at least one metal complex according to the invention and at least one solvent, preferably an organic solvent.

The compounds according to the invention and the organic electroluminescent devices produced therewith are distinguished by the following surprising advantages over the prior art:

In contrast to many metal complexes in accordance with the prior art, which undergo partial or complete pyrolytic decomposition on sublimation, the compounds according to the invention have high thermal stability.

Organic electroluminescent devices comprising compounds of the formula I, II, III, IV or V as emitting materials have an excellent lifetime.

Blue-, red- and green-phosphorescent complexes which have a deep-blue, efficient red or even green emission colour are accessible. In particular in the case of blue-phosphorescent devices, there is still a need for improvement over the prior art, especially with respect to the colour coordinates and the lifetime.

The compounds according to the invention, employed in organic electroluminescent devices, result in high efficiencies and steep current-voltage curves at the same time as a low use voltage.

These above-mentioned advantages are not accompanied by an impairment of the other electronic properties.

The invention is explained in greater detail by the following examples, without wishing to restrict it thereby. The person skilled in the art will be able to synthesise further compounds according to the invention without inventive step and employ them in organic electroluminescent devices.

EXAMPLES

The following syntheses are carried out under a protective-gas atmosphere in dried solvents, unless indicated otherwise. The solvents and reagents can be purchased from ALDRICH or ABCR.

Example 1

Ligand 1

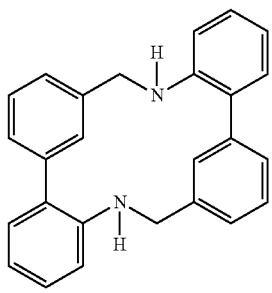 [SMILES: c1cc2cc(c1)-c1ccccc1NCc1cccc(c1)-c1ccccc1NC2]

33.4 g (168 mmol) of 2-amino-3'-hydroxymethylbiphenyl—prepared from 2-aminobiphenyl-3'-carboxylic acid by reduction using lithium aluminium hydride in THF—1.8 g (17 mmol) of benzaldehyde and 1.9 g (34 mmol) of KOH are heated under reflux in 1500 ml of diphenyl ether in an apparatus with air-cooled distillation bridge, and the boiling diphenyl ether is distilled off and replaced continuously by fresh diphenyl ether, where the production of water is complete when 1000 ml of diphenyl ether have been distilled off. The remaining diphenyl ether is substantially distilled off, the residue is taken up in 1000 ml of dichloromethane, washed twice with 500 ml of water, the organic phase is dried over magnesium sulfate, and the dichloromethane is removed in vacuo. The resultant oil is chromatographed on silica gel (eluent dichloromethane), with oligomeric and polymeric components remaining at the start and the product being eluted at Rf=0.6. The diphenyl ether fractions are separated off by recrystallisation of the oily product with warming by addition of 20 ml of ethyl acetate and 100 ml of methanol. Yield: 10.5 g (29 mmol), 34.5%; purity according to $^1$H-NMR about 97%.

Example 2

Ligand 2

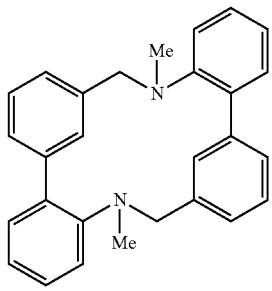 [SMILES: CN1Cc2cccc(c2)-c2ccccc2N(C)Cc2cccc(c2)-c2ccccc21]

A mixture of 3.6 g (10 mmol) of ligand 1, 5.5 g (40 mmol) of potassium carbonate, 7.5 ml (120 mmol) of methyl iodide and 60 ml of acetonitrile is stirred at 50° C. for 24 h. The acetonitrile is removed in vacuo, and the residue is taken up in 200 ml of dichloromethane, washed twice with 100 ml of water and dried over magnesium sulfate. The oil obtained after stripping off the dichloromethane in vacuo is recrystallised from ethyl acetate. Yield: 3.0 g (8 mmol), 83.2%; purity according to $^1$H-NMR about 99%.

Examples 3 to 6

The ligands 3 to 6 shown in Table 2 are obtained analogously to Example 2 using the corresponding bromides or iodides in Examples 3 to 6.

TABLE 2

| Example | Bromide | Ligand | Yield |
|---|---|---|---|
| 3 | (benzyl bromide) | Ligand 3 | 78.3% |
| 4 | (neopentyl bromide) | Ligand 4 | 84.0% |
| 5 | (isopropyl iodide) | Ligand 5 | 62.1% |
| 6 | (2-picolyl bromide) | Ligand 6 | 37.0% |

Example 7

Ligand 7

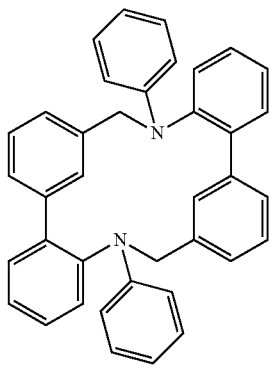 [SMILES: c1ccc(N2Cc3cccc(c3)-c3ccccc3N(c3ccccc3)Cc3cccc(c3)-c3ccccc32)cc1]

457 mg (1.5 mmol) of tri-o-tolylphosphine and 225 mg (1.0 mmol) of palladium(II) acetate are added to a mixture of 9.1 g (25 mmol) of ligand 1, 11.8 g (75 mmol) of bromobenzene, 5.8 g (60 mmol) of sodium tert-butoxide in 200 ml of toluene, and the mixture is heated under reflux for 5 h. After cooling, 200 ml of water are added, the organic phase is separated off, dried over magnesium sulfate and filtered through a Celite bed, the toluene is stripped off in vacuo, and the oil is recrystallised from ethyl acetate/ethanol. Yield: 7.2 g (14 mmol), 56.0%; purity according to $^1$H-NMR about 99%.

Examples 8 and 9

The ligands 8 and 9 shown in Table 3 are obtained analogously to Example 7 using the corresponding bromides in Examples 8 and 9.

TABLE 3

| Example | Bromide | Ligand | Yield |
|---|---|---|---|
| 8 | 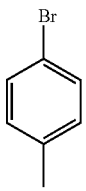 | 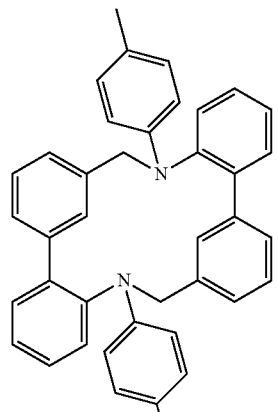 Ligand 8 | 60.1% |
| 9 | 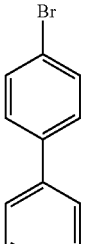 | 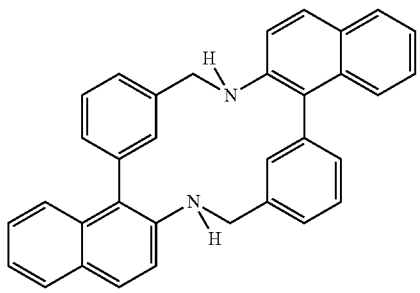 [SMILES: c1cc2cc(c1)-c1c(ccc3ccccc13)NCc1cccc(c1)-c1c(ccc3ccccc13)NC2] Ligand 9 | 84.0% |

Example 10

Ligand 10

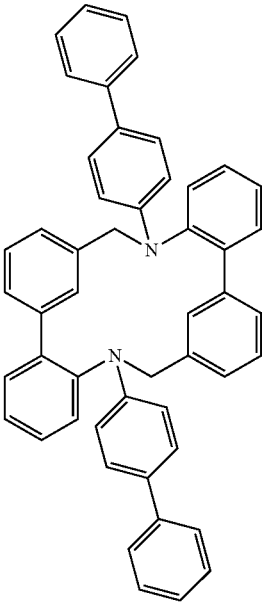

A: 3-(2-Aminonaphthalen-1-yl)benzoic acid

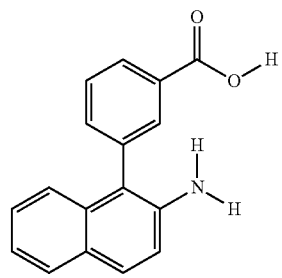 [SMILES: Nc1ccc2ccccc2c1-c1cccc(C(=O)O)c1]

A freshly prepared solution of 112 mg (0.5 mmol) of palladium(II) acetate, 106 mg (1 mmol) of sodium carbonate and 186 mg (0.5 mmol) of ethylenediaminetetraacetic acid disodium dihydrate in 50 ml of water is added to a vigorously stirred mixture of 22.2 g (100 mmol) of 1-bromo-2-aminonaphthalene [20191-75-7], 18.3 g (110 mmol) of 3-carboxybenzeneboronic acid [25487-66-5], 27.6 g (200 mmol) of potassium carbonate and 645 mg (2 mmol) of tetrabutylammonium bromide in 300 ml of water, and the mixture is heated under reflux for 16 h. After cooling, the pH is adjusted to 3-4 by addition of acetic acid, and the solid is filtered off with suction, washed a number of times with 5% by weight acetic acid, dried in vacuo and then subjected to azeotropic drying with toluene. Yield: 23.8 g (90 mmol), 90.4%; purity according to $^1$H-NMR about 98%.

B: 3-(2-Aminonaphthalen-1-yl)phenylmethanol

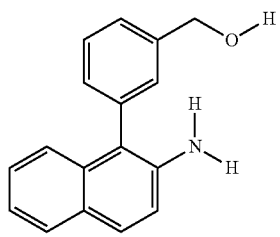 [SMILES: Nc1ccc2ccccc2c1-c1cccc(CO)c1]

A solution of 13.2 g (50 mmol) of 3-(2-aminonaphthalen-1-yl)benzoic acid in 300 ml of THF is added dropwise to a solution of 3.8 g (100 mmol) of lithium aluminium hydride in 500 ml of THF. When the addition is complete, the mixture is stirred under reflux for a further 2 h and allowed to cool, 4 ml of water, 4 ml of 15% by weight NaOH solution and 12 ml of water are then added dropwise, the mixture is stirred for a further 30 min., the precipitated salts are filtered off with suction and washed three times with 100 ml of THF each time, and the THF is removed in vacuo. Yield: 11.2 g (90 mmol), 89.8%; purity according to $^1$H-NMR about 95%.

C: Ligand 10

Preparation analogous to Ex. 1, using 100 mmol of 3-(2-aminonaphthalen-1-yl)phenylmethanol instead of 168 mmol of 2-amino-3'-hydroxymethylbiphenyl and adapting the other reagents and solvents proportionally. Yield: 6.4 g (14 mmol), 27.7%; purity according to $^1$H-NMR about 99%.

Example 11

Ligand 11

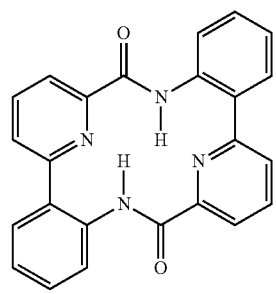 [SMILES: O=c1[nH]c2ccccc2c2cccc(n2)c(=O)[nH]c2ccccc2c2cccc1n2]

A: 6-(2-Aminophenyl)pyridine-2-carboxylic acid

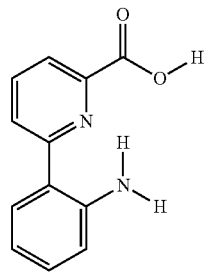 [SMILES: Nc1ccccc1-c1cccc(C(=O)O)n1]

Preparation analogous to Ex. 10, A, using 110 mmol of 2-aminophenylboronic acid [5570-18-3] instead of 110 mmol of 3-carboxybenzeneboronic acid, and using 100 mmol of 6-bromopyridine-2-carboxylic acid [21190-87-4] instead of 100 mmol of 1-bromo-2-aminonaphthalene. Yield: 17.5 g (82 mmol), 81.7%; purity according to $^1$H-NMR about 99%.

C: Ligand 11

A solution of 10.3 g (50 mmol) of dicyclohexylcarbodiimide in 100 ml of DMSO is added dropwise to a solution of 5.4 g (25 mmol) of 6-(2-aminophenyl)pyridine-2-carboxylic acid and 12.2 g (100 mmol) of 4-dimethylaminopyridine, and the mixture is subsequently stirred at room temperature for 20 h. The solvent is removed in vacuo, the residue is taken up in 300 ml of ethyl acetate, the organic phase is washed three times with 200 ml of water each time, and the solvent is removed in vacuo. The residue is chromatographed on silica gel using ethyl acetate:methanol 3:1. Yield: 872 mg (2 mmol), 17.8%; purity according to $^1$H-NMR about 99%.

Example 12

Ligand 12

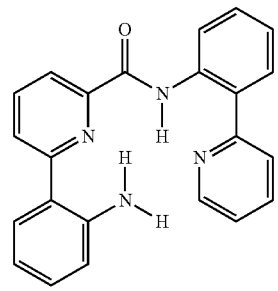 [SMILES: Nc1ccccc1-c1cccc(C(=O)Nc2ccccc2-c2ccccn2)n1]

A solution of 6.2 g (30 mmol) of dicyclohexylcarbodiimide in 100 ml of DMSO is added dropwise to a solution of 5.4 g (25 mmol) of 6-(2-aminophenyl)pyridine-2-carboxylic acid, 17.0 g (100 mmol) of 2-(2-pyridyl)aniline [29528-30-1] and 12.2 g (100 mmol) of 4-dimethylaminopyridine, and the mixture is subsequently stirred at room temperature for 20 h. The solvent is removed in vacuo, the residue is taken up in 300 ml of ethyl acetate, the organic phase is washed three times with 200 ml of water each time, and the solvent is removed in vacuo. The residue is chromatographed on silica gel using ethyl acetate:methanol 3:1. Yield: 4.7 g (51 mmol), 51.3%; purity according to $^1$H-NMR about 99%.

Example 13

Pt-ligand 2

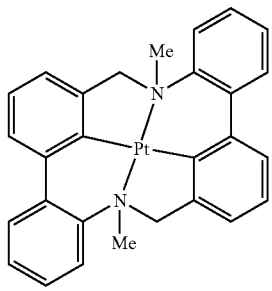

A suspension of 3.9 g (10 mmol) of ligand 2, 4.2 g (10 mmol) of dipotassium tetrachloroplatinate(II) and 3.3 g (50 mmol) of lithium acetate in 50 ml of glacial acetic acid is heated under reflux for 60 h. After cooling, the glacial acetic acid is removed in vacuo, and the residue is dissolved in dichloromethane and chromatographed on silica gel using dichloromethane. The resultant solid is subsequently recrystallised from dichloromethane/hexane and then sublimed in vacuo (p=1×10$^{-5}$ mbar, T=330° C.). Yield: 675 mg (1.1 mmol), 11.5%; purity 99.9% according to HPLC.

Examples 14 to 19

The following platinum complexes are obtained analogously from the corresponding ligands.

TABLE 4

| Example | Ligand | Platinum complex | Yield |
|---|---|---|---|
| 14 | Ligand 4 | Pt-ligand 4 | 15.7% |
| 15 | Ligand 5 | Pt-ligand 5 | 9.0% |
| 16 | Ligand 7 | Pt-ligand 7 | 16.1% |

TABLE 4-continued
| Example | Ligand | Platinum complex | Yield |
|---|---|---|---|
| 17 | 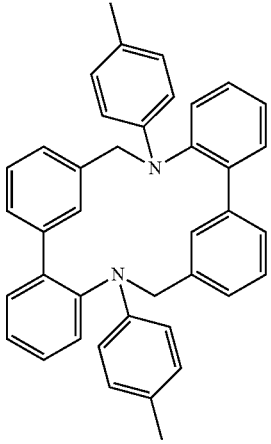<br>Ligand 8 | 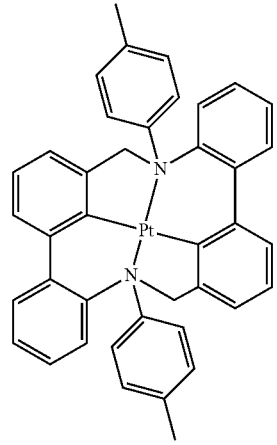<br>Pt-ligand 8 | 17.8% |
| 18 | 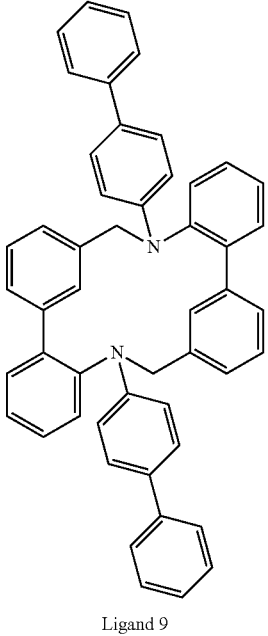 [SMILES: c1ccc(-c2ccc(N3Cc4cccc(c4)-c4ccccc4N(c4ccc(-c5ccccc5)cc4)Cc4cccc(c4)-c4ccccc43)cc2)cc1]<br>Ligand 9 | 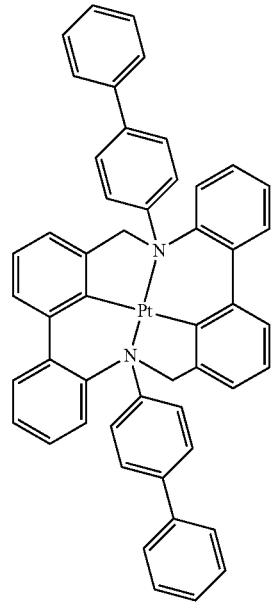<br>Pt-ligand 9 | 11.4% |
| 19 | 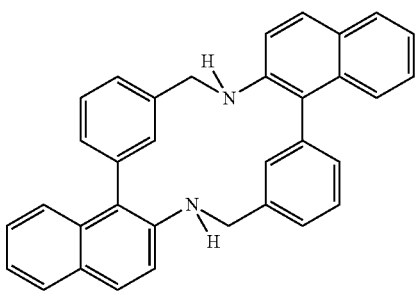<br>Ligand 10 | 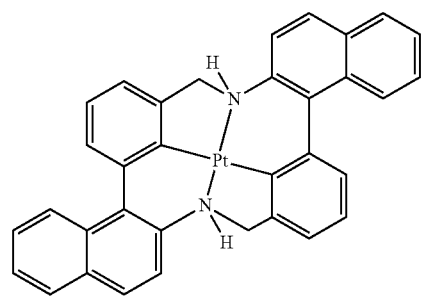<br>Pt-ligand 10 | 4.6% |

Example 20

Pt-ligand 11

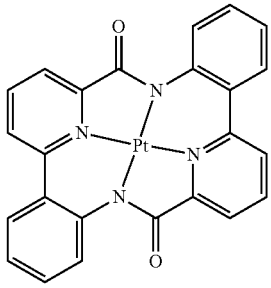

12.5 ml (20 mmol) of n-butyllithium (1.6 M in hexane) are added dropwise to a solution, cooled to −10° C., of 3.9 g (10 mmol) of ligand 11 in 100 ml of THF, and the mixture is stirred at −10° C. for a further 30 min. A solution of 4.7 g (10 mmol) of bisbenzonitrileplatinum(II) chloride in 50 ml of THF is then added dropwise, and the mixture is allowed to warm to room temperature and stirred for a further 24 h. The THF is removed in vacuo, and the residue is chromatographed on silica gel using acetone. The resultant solid is subsequently recrystallised from acetone/hexane and then sublimed in vacuo ($p=1\times10^{-5}$ mbar, T=340° C.). Yield: 920 mg (1.6 mmol), 15.7%; purity 99.9% according to HPLC.

Example 21

Pt-ligand 12

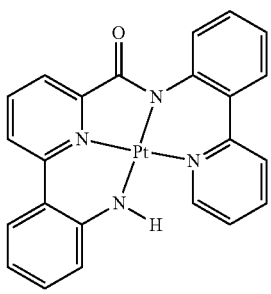

12.5 ml (20 mmol) of n-butyllithium (1.6 M in hexane) are added dropwise to a solution, cooled to −10° C., of 3.7 g (10 mmol) of ligand 12 in 200 ml of THF, and the mixture is stirred at −10° C. for a further 30 min. A solution of 4.7 g (10 mmol) of bisbenzonitrileplatinum(II) chloride in 50 ml of THF is then added dropwise, and the mixture is allowed to warm to room temperature and stirred for a further 24 h. The THF is removed in vacuo, and the residue is chromatographed on silica gel using acetone. The resultant solid is subsequently recrystallised from acetone/hexane and then sublimed in vacuo ($p=1\times10^{-5}$ mbar, T=340° C.). Yield: 1.4 g (2.5 mmol), 25.0%; purity 99.9% according to HPLC.

Example 22

Pt-ligand 2 $(CN)_2$

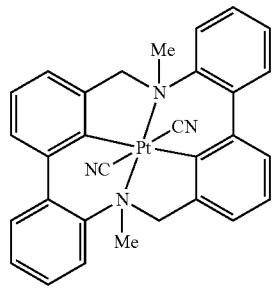

10 ml of a 0.1 M solution of bromine in dichloromethane are added dropwise to a solution of 584 mg (1.0 mmol) of Pt-ligand 2 in 50 ml of dichloromethane, and the mixture is then stirred at room temperature for 2 h. The dichloromethane is removed in vacuo, the residue is taken up in 5 ml of DMSO, 293 mg (6 mmol) of sodium cyanide are added, the mixture is stirred at 80° C. for 24 h and allowed to cool, and 50 ml of methanol are then added with stirring. The precipitated solid is filtered off with suction, washed three times with 5 ml of methanol each time and dried in a high vacuum ($p=1\times10^{-5}$ mbar, T=200° C.). Yield: 473 mg (0.7 mmol), 74.4%; purity 99.5% according to HPLC.

Production and Characterisation of Organic Electroluminescent Devices Comprising the Compounds According to the Invention Electroluminescent devices according to the invention can be produced as described in general terms, for example, in WO 05/003253. The results for various OLEDs are compared here. The basic structure, the materials used, the degree of doping and their layer thicknesses are identical for better comparability.

Device Example 23 describes the comparative standard in accordance with the prior art, in which the emission layer consists of the host material (or matrix) 3,6-bis-N-carbazolyldibenzofuran M and the blue-emitting guest material (dopant) 10% of fac-tris[2-(2-pyridinyl)(5-cyanophenyl)]iridium(III) TEB 1.

Furthermore, OLEDs having an identical structure and comprising the dopant according to the invention from the examples mentioned above are described (Device Examples 24 to 33). The following device structure is used here:

| | |
|---|---|
| Hole-injection layer (HIL) | 20 nm of 2,2',7,7'-tetrakis(di-para-tolyl-amino)spiro-9,9'-bifluorene; |
| Hole-transport layer (HTL) | 5 nm of NPB (N-naphthyl-N-phenyl-4,4'-diaminobiphenyl); |
| Electron-blocking layer (EBL) | 15 nm of EBL (9,9-bis-(3,5-diphenyl-aminophenyl)fluorene); |
| Emission layer (EML) | 40 nm of host material: 3,6-bis-N-carbazolyldibenzofuran M; |
| Dopant | 10% by vol. doping; compounds see Table 5; |
| Electron conductor (ETL) | 20 nm of BAlq; |
| Cathode | 1 nm of LiF, 100 nm of Al on top. |

The structures of EBL, M and TEB are depicted below for clarity.

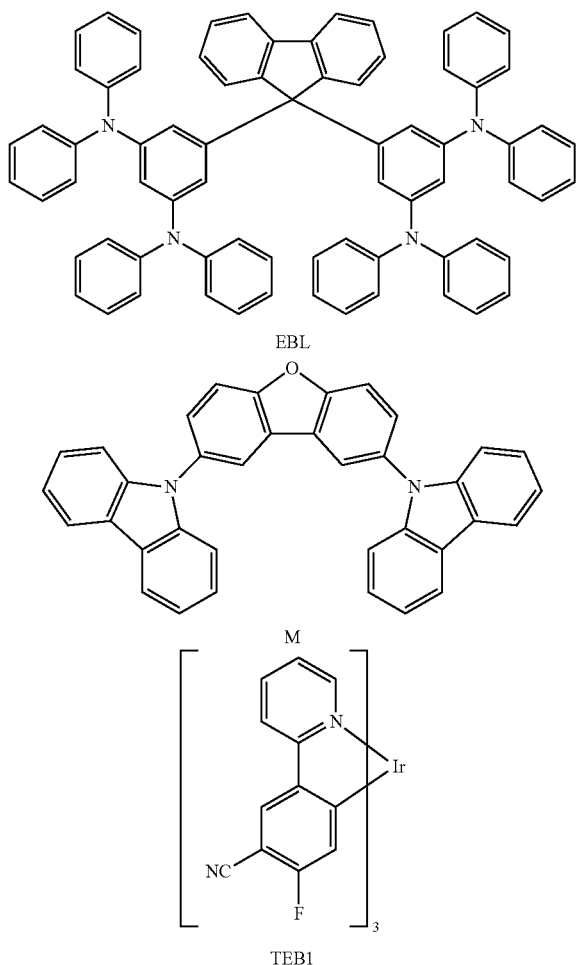

EBL

M

TEB1

For characterisation of these OLEDs, the electroluminescence spectra, the external quantum efficiency (measured in %) as a function of the luminance, calculated from current-voltage-luminance characteristic lines (IUL characteristic lines), are determined.

As can be seen from Table 5, the electroluminescent devices according to the invention exhibit comparable or superior behaviour to the comparative devices comprising the dopant TEB 1 in accordance with the prior art in the external quantum efficiencies (EQEs), voltages and colour coordinates.

TABLE 5

| Device Example | Dopant | EQE at 100 cd/m² [%] | Voltage at 100 cd/m² [V] | CIE x/y |
|---|---|---|---|---|
| 23 comparison | TEB 1 | 8.3 | 6.6 | 0.16/0.25 |
| 24 | Pt-ligand 2 (from Ex. 13) | 11.2 | 6.1 | 0.15/0.23 |
| 25 | Pt-ligand 4 (from Ex. 14) | 7.2 | 6.9 | 0.15/0.23 |
| 26 | Pt-ligand 5 (from Ex. 15) | 8.1 | 6.7 | 0.16/0.25 |
| 27 | Pt-ligand 7 (from Ex. 16) | 9.0 | 5.9 | 0.17/0.26 |

TABLE 5-continued

| Device Example | Dopant | EQE at 100 cd/m² [%] | Voltage at 100 cd/m² [V] | CIE x/y |
|---|---|---|---|---|
| 28 | Pt-ligand 8 (from Ex. 17) | 8.8 | 6.1 | 0.16/0.25 |
| 29 | Pt-ligand 9 (from Ex. 18) | 9.1 | 5.7 | 0.16/0.26 |
| 30 | Pt-ligand 10 (from Ex. 19) | 12.3 | 5.4 | 0.32/0.65 |
| 31 | Pt-ligand 11 (from Ex. 20) | 3.1 | 7.9 | 0.22/0.54 |
| 32 | Pt-ligand 12 (from Ex. 21) | 1.6 | 8.1 | 0.23/0.51 |
| 33 | Pt-ligand 2 (CN)₂ (from Ex. 22) | 0.9 | 7.9 | 0.14/0.17 |

The invention claimed is:

1. A compound of the general formula I

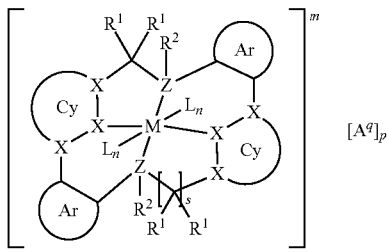

formula I wherein the symbols and indices have the following meanings:

M is Mo, W, Ru, Os, Rh, Ir, Ni, Pd, Pt, Cu, Ag, Au, Zn, or in that the metal M is a main-group metal or main-group metal ion, alkali metals, alkaline-earth metals, Al, Ga or In;

L is, identically or differently on each occurrence, a neutral, cationic or anionic ligand;

X is, identically or differently on each occurrence, C or N;

Z is, identically or differently on each occurrence, N or P;

Cy is, identically or differently on each occurrence, an aryl or heteroaryl group or a cyclic carbene, in each case having 5 to 16 ring atoms, which is selected from the group consisting of phenyl, naphthyl, anthracyl, phenanthryl, biphenyl, pyridyl, 1,3-diazolyl, 1,3-diazocyclopentyl and benzo-1,3-diazolyl, each of which is optionally substituted by one or more radicals $R^1$;

Ar is, identically or differently on each occurrence, a mono- or polycyclic aryl or heteroaryl group having 5 to 60 ring atoms, which is optionally substituted by one or more radicals $R^1$, with the proviso that the C atoms which bond to X or Z are constituents of the group Ar;

$R^1$ is, identically or differently on each occurrence, and are H, D, F, Cl, Br, I, CN, $NO_2$, a straight-chain $C_{1-40}$-alkyl group, $C_{1-40}$-alkoxy group, thio-$C_{1-40}$-alkyl group, a branched or cyclic $C_{3-40}$-alkyl group, $C_{3-40}$-alkoxy group or thio-$C_{3-40}$-alkoxy group, each of which is optionally substituted by one or more radicals $R^3$, where one or more non-adjacent $CH_2$ groups is optionally replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, $SO$, $SO_2$, $NR^5$, $O$, $S$ or $CONR^5$, and where one or more H atoms is optionally replaced by D, F, Cl, Br, I, CN or $NO_2$, a mono- or polycyclic aromatic or heteroaromatic ring system having 5 to 60 aromatic ring atoms, which may in each case be substituted by one or more radicals $R^4$, where, in the case where two adjacent $R^1$ in each case form an aromatic or heteroaromatic ring system, these two ring systems is optionally linked to one another by a single bond or a divalent unit G, an aryloxy or heteroaryloxy group having 5 to 60 aromatic ring atoms, which is optionally substituted by one or more radicals $R^4$, and a combination of these groups, where one of the $R^1$ is optionally linked to an L, forming a penta- or hexadentate ligand; or where one of the $R^1$ is optionally linked to an L and an opposite $R^1$ or $R^2$, forming a penta- or hexadentate ligand in the form of a cage;

or two adjacent $R^1$ together form an oxo group =O, a group =NH or a group =$NR^5$, or two adjacent $R^1$, together with the atom or atoms to which they are bonded, form a 5- or 6-membered aliphatic or aromatic ring, which is optionally substituted by one or more radicals $R^4$, where one or more of the ring $CH_2$ groups is optionally replaced by O, S or $NR^2$;

$R^2$ is, identically or differently on each occurrence, and are a non-bonding electron pair, H, D, a straight-chain $C_{1-40}$-alkyl group, $C_{1-40}$-alkoxy group or thio-$C_{1-40}$-alkyl group or a branched or cyclic $C_{3-40}$-alkyl group, $C_{3-40}$-alkoxy group or thio-$C_{3-40}$-alkoxy group, each of which is optionally substituted by one or more radicals $R^3$, where one or more non-adjacent $CH_2$ groups is optionally replaced by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$, and where one or more H atoms is optionally replaced by D, F, Cl, Br, I, CN or $NO_2$, a mono- or polycyclic aromatic or heteroaromatic ring system having 5 to 60 ring atoms, which may in each case be substituted by one or more radicals $R^4$, an aryloxy or heteroaryloxy group having 5 to 60 aromatic ring atoms, which is optionally substituted by one or more radicals $R^4$, and a combination of these groups; or in the case where Z is equal to N, $R^2$ may furthermore be equal to O, in which case an amine oxide is formed;

$R^3$ is, identically or differently on each occurrence, a mono- or polycyclic aromatic or heteroaromatic ring system having 5 to 30 ring atoms, in which one or more H atoms is optionally replaced by D, F, Cl, Br, I, CN or $NO_2$, where, in the case where two adjacent $R^3$ in each case form an aromatic or heteroaromatic ring system, these two ring systems is optionally linked to one another by a single bond or a divalent unit G;

$R^4$ is, identically or differently on each occurrence, and are a straight-chain $C_{1-20}$-alkyl group or a branched or cyclic $C_{3-20}$-alkyl group, or two adjacent $R^4$, together with the atoms to which they are bonded, form a 5-, 6-, 7- or 8-membered aliphatic ring, where one or more of the ring $CH_2$ groups is optionally replaced by O, S or $NR^2$;

$R^5$ is selected, identically or differently on each occurrence, and are H, D, a straight-chain $C_{1-20}$-alkyl group or a branched or cyclic $C_{3-20}$-alkyl group, in which in each case one or more H atoms is optionally replaced by D, F, Cl, Br, I, CN or $NO_2$, a mono- or polycyclic aromatic or heteroaromatic ring system having 5 to 30 ring atoms, in which one or more H atoms is optionally replaced by D, F, Cl, Br, I, CN or $NO_2$, where, in the case where two adjacent $R^5$ in each case form an aromatic or heteroaromatic ring system, these two ring systems is optionally linked to one another, or two adjacent $R^5$, together with the atoms to which they are bonded, form a 5-, 6-, 7- or 8-membered aliphatic ring, where one or more of the ring $CH_2$ groups is optionally replaced by O, S or NH;

G represents a divalent unit which is selected from the group consisting of $C(R^5)_2$—, $C(R^5)_2$—$C(R^5)_2$, C=O, $NR^5$, $PR^5$, O and S;

n is, identically or differently on each occurrence, 0 or 1;

m denotes the charge of the complex and can be +4, +3, +2, +1, 0, −1, −2, −3 or −4;

$A^q$ is a counterion, where q represents the charge of A and can be −4, −3, −2, −1, 0, +1, +2, +3 or +4;

p is 0, 1, 2, 3 or 4;

s is 0 or 1, where, for s=0, a further group $R^2$ is also bonded to the corresponding Z and a group $R_1$ is also bonded to the corresponding X.

2. The compound according to claim 1, wherein the unit Ar is a unit selected from the group consisting of phenyl, naphthyl, anthracyl, phenanthryl and pyridyl, each of which is optionally substituted by one or more radicals $R^1$.

3. The compound according to claim 1, in which the compound of the formula I is a compound of the following formula II:

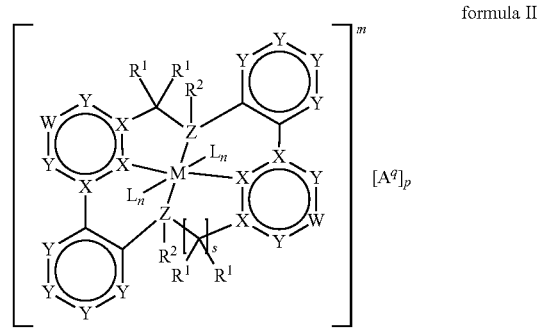

formula II where the symbols M, L, X, Z, A, $R^1$ and $R^2$ and the indices n, m, p, q and s have the same meanings as defined in claim 1, and the other symbols have the following meanings:

Y is, identically or differently on each occurrence, $CR^6$ or N; or precisely one Y per ring is $NR^6$, S or O if the group W in this ring stands for a bond;

W is, identically or differently on each occurrence, either not present, so that a covalent bond is formed between the two Y bonded to W, or is $CR^6$ or N, with the proviso that a maximum of two representatives from the unit formed from Y—W—Y can be nitrogen atoms;

$R^6$ is, identically or differently on each occurrence, and are H, D, F, Cl, Br, I, CN, $NO_2$, a $C_{1-10}$-alkyl group, in which one or more 1H atoms is optionally replaced by F, a $C_{6-18}$-aryl group or $C_{1-18}$-heteroaryl group, each of which may carry one or more $C_{1-6}$-alkyl groups as substituents, a 5- to 18-membered heteroaryl group, a $C_{1-10}$-alkoxy group, a $C_{6-18}$-aryloxy group and a 5- to 18-membered heteroaryloxy group, or two $R^6$ in the vicinal position form a divalent group —$CR^7$=$CR^7$—$CR^7$=$CR^7$— with one another, or two $R^6$ in the vicinal position are linked to one another with formation of an aliphatic ring system;

$R^7$ is, identically or differently on each occurrence, and are H, D, F, Cl, Br, I, CN, $NO_2$, a $C_{1-10}$-alkyl group, in which one or more H atoms is optionally replaced by F, a $C_{6-18}$-aryl group, which may carry a $C_{1-6}$-alkyl group as substituent, a 5- to 18-membered heteroaryl group, a $C_{1-10}$-alkoxy group, a $C_{6-18}$-aryloxy group and a 5- to 18-membered heteroaryloxy group, or two $R^7$ in the vicinal position form a divalent group —$CR^8$=$CR^8$— $CR$=$CR^8$— with one another;

$R^8$ is, identically or differently on each occurrence, and are H, D, F, Cl, Br, I, CN, $NO_2$, a $C_{1-10}$-alkyl group, in which one or more H atoms may be replaced by F, a $C_{6-18}$-aryl group, which may carry a $C_{1-6}$-alkyl group as substituent, a 5- to 18-membered heteroaryl group, a $C_{1-10}$-alkoxy group, a $C_{6-18}$-aryloxy group or a 5- to 18-membered heteroaryloxy group.

4. The compound according to claim 1, in which the compound of the formula I is a compound of the following formula III, IV or V:

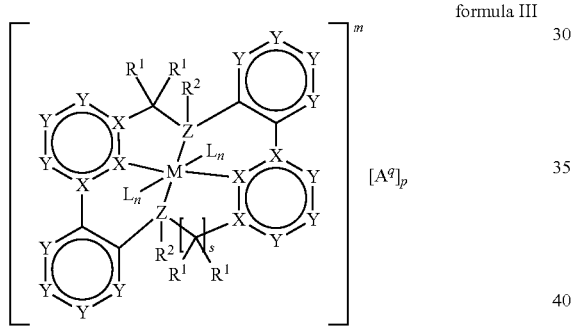

formula III where the symbols M, L, X, Y, Z, A, $R^1$ and $R^2$ and the indices n, m, p, q and s have the same meanings as defined in claim 1, and Y stands, identically or differently on each occurrence, for $CR^6$;

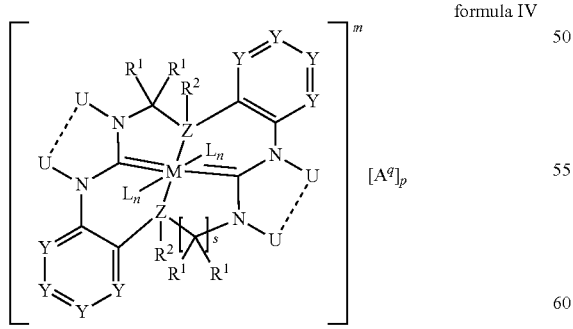

formula IV where the symbols M, L, Y, Z, A, $R^1$ and $R^2$ and the indices n, m, p, q and s have the same meanings as defined claim 1, and the dashed lines represent either a single covalent bond or a double covalent bond, where, in the case where the dashed line represents a single covalent bond, U is in each case a $CH_2$ or $C(R^5)_2$ unit, and, in the case where the dashed line represents a double covalent bond, U is a $CR^6$ unit, where $R^5$ and $R^6$ are as defined in claim 1;

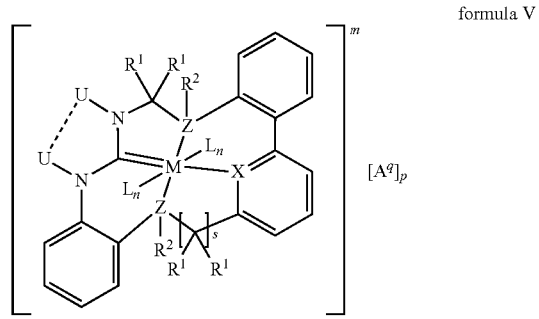

formula V where the symbols M, I, Z, X, A, $R^1$ and $R^2$ and the indices n, m, p, q and s have the same meanings as defined above, and U is equal to $CR^6$, where $R^6$ is as defined above.

5. The compound according to claim 1, wherein the symbol X, which coordinates to the metal, is equal to N, Z is equal to N, $R^2$ is a non-bonding electron pair, and M is equal to Pt, or in that the symbol X, which coordinates to the metal, is equal to C and M is equal to Pt.

6. The compound according to claim 1, wherein the ligand L is selected, identically or differently on each occurrence, from the group consisting of the following:

CO, NO, SH, OH, carbenes, isonitriles, amines, phosphines, phosphites, arsines, stibines, nitrogen-containing heterocycles, hydride, deuteride, F, Cl, Br, I, alkylacetylides, arylacetylides, heteroarylacetylides, cyanide, cyanate, isocyanate, thiocyanate, isothiocyanate, aliphatic or aromatic alcoholates, aliphatic or aromatic thioalcoholates, amides, carboxylates, anionic nitrogen-containing heterocycles and anionic aromatic compounds;

or in that $R^1$ and L together form a unit which is selected from the group consisting of the following:

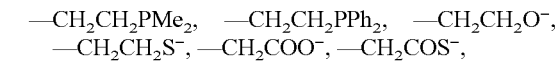

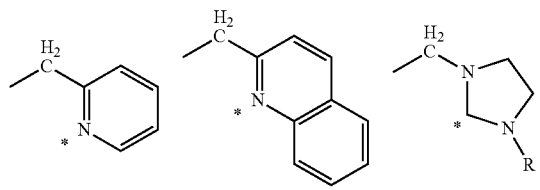

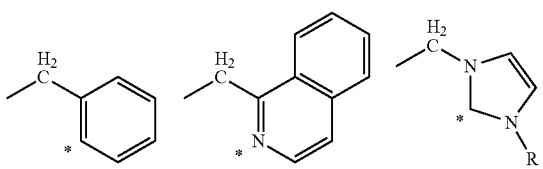

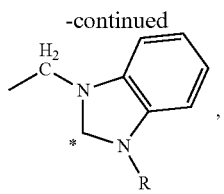

wherein the position denoted by * is coordinated to the metal M.

7. An oligomer, polymer or dendrimer comprising one or more compounds according to claim 1, where one or more bonds are present from the compounds of the formula I to the polymer, oligomer or dendrimer.

8. A process for the preparation of the compound according to claim 1, which comprises reacting a free ligand with a corresponding metal salt to give the complex.

9. A layer comprising at least one compound according to claim 1.

10. An organic electroluminescent device wherein the compound according to claim 1 is employed as emitting compound in an emitting layer or as charge-transport compound in a charge-transport layer or charge-injection layer.

11. A formulation comprising one or more compounds according to claim 1 and at least one solvent.

12. An electronic device comprising one or more compounds according to claim 1.

13. The electronic device as claimed in claim 12, wherein the device is an organic electroluminescent device or polymeric electroluminescent device (OLED, PLED), organic integrated circuit (O-IC), organic field-effect transistor (O-FET), organic thin-film transistor (O-TFT), organic light-emitting transistor (O-LET), organic solar cell (O-SC), organic optical detector, organic photoreceptor, organic field-quench device (O-FQD), light-emitting electrochemical cell (LEC) or organic laser diode (O-laser).

14. The electronic device as claimed in claim 13, wherein the device is an organic electroluminescent device.

15. A compound of the general formula Ia:

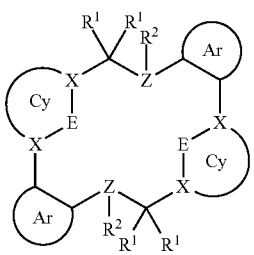

formula Ia

X is, identically or differently on each occurrence, C or N;
Z is, identically or differently on each occurrence, N or P;
Cy is, identically or differently on each occurrence, an aryl or heteroaryl group or a cyclic carbene, in each case having 5 to 16 ring atoms which is selected from the group consisting of phenyl, naphthyl, anthracyl, phenanthryl, biphenyl, pyridyl, 1,3-diazolyl, 1,3-diazocyclopentyl and benzo-1,3-diazolyl, each of which is optionally substituted by one or more radicals $R^1$;
Ar is, identically or differently on each occurrence, a mono- or polycycli aryl or heteroarvl group having 5 to 60 ring atoms, which is optionally substituted by one or more radicals $R^1$, with the proviso that the C atoms which bond to X or Z are constituents of the group Ar;
$R^1$ is, identically or differently on each occurrence, and are H, D, F, Cl, Br, I, CN, $NO^2$, a straight-chain $C_{1-40}$-alkyl group, $C_{1-40}$alkoxyy group, thio $C_{1-40}$-alkyl group, a branched or cyclic $C_{3-40}$-alkyl group, $C_{3-40}$-alkoxy group or thio-$C_{3-40}$-alkoxy group, each of which is optionally substituted by one or more radicals $R^3$, where one or more non-adjacent $CH_2$ groups is optionally replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$, and where one or more H atoms is optionally replaced by D, F, Cl, Br, I, CN or $NO_2$, a mono- or polycyclic aromatic or heteroaromatic ring system having 5 to 60 aromatic ring atoms, which may in each case be substituted by one or more radicals $R^4$, where, in the case where two adjacent $R^1$ in each case form an aromatic or heteroaromatic ring system, these two ring systems is optionally linked to one another by a single bond or a divalent unit G, an aryloxy or heteroaryloxy group having 5 to 60 aromatic ring atoms, which is optionally substituted by one or more radicals $R^4$, and a combination of these groups, where one of the $R^1$ is optionally linked to an I, forming a penta- or hexadentate ligand; or where one of the $R^1$ is optionally linked to an L and an opposite $R^1$ or $R^2$, forming a penta- or hexadentate ligand in the form of a cage; or two adjacent $R^1$ together form an oxo group =O, a group =NH or a group $=NR^5$, or two adjacent $R^1$, together with the atom or atoms to which they are bonded, form a 5- or 6-membered aliphatic or aromatic ring, which is optionally substituted by one or more radicals $R^4$, where one or more of the ring $CH_2$ groups is optionally replaced by O, S or $NR^2$;

$R^2$ is, identically or differently on each occurrence, and are a non-bonding electron pair, H, D, a straight-chain $C_{1-40}$-alklyl group, $C_{1-40}$-alkoxy group or thio-$C_{1-40}$-alkyl group or a branched or cyclic $C_{1-40}$-alkyl group, $C_{3-40}$-alkoxy group or thio-$C_{3-40}$-alkoxy group, each of which is optionally substituted by one or more radicals $R^3$, where one or more non-adjacent $CH_2$ groups is optionally replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$, and where one or more H atoms is optionally replaced by D, F, Cl, Br, I, CN or $NO_2$, a mono- or polycyclic aromatic or heteroaromatic ring system having 5 to 60 ring atoms, which may in each case be substituted by one or more radicals $R^4$, an aryloxy or heteroaryloxy group having 5 to 60 aromatic ring atoms, which is optionally substituted by one or more radicals $R^4$, and a combination of these groups; or in the case where Z is equal to N, $R^2$ may furthermore be equal to O, in which case an amine oxide is formed;

$R^3$ is, identically or differently on each occurrence, a mono- or polycyclic aromatic or heteroaromatic ring system having 5 to 30 ring atoms, in which one or more H atoms is optionally replaced by D, F, Cl, Br, I, CN or $NO_2$, where, in the case where two adjacent $R^3$ in each case form an aromatic or heteroaromatic ring system, these two ring systems is optionally linked to one another by a single bond or a divalent unit G;

$R^4$ is, identically or differently on each occurrence, and are a straight-chain $C_{1-20}$-alkyl group or a branched or cyclic $C_{3-20}$-alkyl group
or
two adjacent $R^4$, together with the atoms to which they are bonded, form a 5-, 6-, 7- or 8-membered aliphatic ring,
where one or more of the ring $CH_2$ groups is optionally replaced by O, S or $NR^2$;

$R^5$ is selected, identically or differently on each occurrence, and are H, D, a straight-chain $C_{1-20}$-alkyl group or a branched or cyclic $C_{3-20}$-alkyl group, in which in each case one or more H atoms is optionally replaced by D, F, Cl, Br, I, CN or $NO_2$, a mono- or polycyclic aromatic or heteroaromatic ring system having 5 to 30 ring atoms, in which one or more H atoms is optionally replaced by D, F, Cl, Br, I, CN or $NO_2$, where, in the case where two adjacent $R^5$ in each case form an aromatic or heteroaromatic ring system, these two ring systems is optionally linked to one another, or
two adjacent $R^5$, together with the atoms to which they are bonded, form a 5-, 6-, 7- or 8-membered aliphatic ring, where one or more of the ring CH groups is optionally replaced by O, S or NH;

G represents a divalent unit which is selected from the group consisting of $C(R^5)_2$—, —$C(R^5)_2$—$C(R^5)_2$, C=O, $NR^5$, $PR^5$, O and S; and E stands, identically or differently on each occurrence, for CH or N.

\* \* \* \* \*